(12) United States Patent
Fralick et al.

(10) Patent No.: US 8,117,044 B2
(45) Date of Patent: Feb. 14, 2012

(54) BIO-PHOTONIC FEEDBACK CONTROL SOFTWARE AND DATABASE

(75) Inventors: John Fralick, Salt Lake City, UT (US); Kathy L. Chapman, legal representative, Salt Lake City, UT (US); David L. Breiter, Orem, UT (US); Jack Peterson, Provo, UT (US); Mindy Gilbert, Cedar Hills, UT (US); Marvin Distel, Albuquerque, NM (US); Ryan Newman, Elk Ridge, UT (US); Joel Erickson, Spanish Fork, UT (US)

(73) Assignee: NSE Products, Inc., Provo, UT (US)

( * ) Notice: Subject to any disclaimer, the term of this patent is extended or adjusted under 35 U.S.C. 154(b) by 0 days.

(21) Appl. No.: 12/958,506

(22) Filed: Dec. 2, 2010
(Under 37 CFR 1.47)

(65) Prior Publication Data

US 2011/0320324 A1    Dec. 29, 2011

Related U.S. Application Data

(63) Continuation of application No. 10/782,733, filed on Feb. 19, 2004, now abandoned.

(60) Provisional application No. 60/448,996, filed on Feb. 20, 2003.

(51) Int. Cl.
*G06Q 10/00* (2006.01)

(52) U.S. Cl. ............... 705/2; 702/27; 600/300; 600/310; 600/473; 600/478; 600/424; 600/407

(58) Field of Classification Search .......... 600/473–478, 600/424, 407, 300, 310; 705/14, 26, 77, 705/2; 702/27

See application file for complete search history.

(56) References Cited

U.S. PATENT DOCUMENTS 3,272,766 A    9/1966    Gowman
(Continued)

FOREIGN PATENT DOCUMENTS

EP    0 368 436    5/1990
(Continued)

OTHER PUBLICATIONS

API-American Polarizers, Inc., Linear Polarizers, Near Linear Polarizer-HR, http://www.apioptics.com/linear12.htm., pp. 1-4 (Feb. 3, 2004).

(Continued)

*Primary Examiner* — Brian Casler
*Assistant Examiner* — Joel Lamprecht
(74) *Attorney, Agent, or Firm* — Dorsey & Whitney LLP

(57) ABSTRACT

A process, apparatus, and method for computerized detection, tracking, and feedback control of nutritional supplements in an animal, including humans relies on Raman scattering effects on skin or other tissues to determine the content of carotenoids or other nutrients as evidenced in that skin. Serum levels of nutrients may vary dramatically with time, but skin tissues may average such nutrition over time. Skin and other tissues may be scanned with light to produce accurate measurements of carotenoids or other nutrients accumulated in the skin based on the Raman scattering affect of those nutrients in the skin. A score can be derived from a properly calibrated bio-photonic scanner to reflect an averaged effective uptake of the detected nutrient (e.g. such as the carotenoid example). This feedback control is thus much more immediate than any anecdotal, long-term, report of general well being, which would vary so much between individuals as to be nearly impossible to ascertain on an individual level, and difficult, invasive, and expensive to determine individually in a conventional clinical procedure.

7 Claims, 13 Drawing Sheets

U.S. PATENT DOCUMENTS

| | | | |
|---|---|---|---|
| 4,252,709 | A | 2/1981 | Skostins |
| 4,318,057 | A | 3/1982 | Buchwald et al. |
| 4,500,995 | A | 2/1985 | White |
| 4,758,081 | A | 7/1988 | Barnes |
| 4,807,240 | A | 2/1989 | Goldstone |
| 4,832,483 | A | 5/1989 | Verma |
| 4,852,579 | A | 8/1989 | Gilstad et al. |
| 4,858,238 | A | 8/1989 | Cardimona |
| 4,975,581 | A | 12/1990 | Robinson et al. |
| 5,034,228 | A | 7/1991 | Meybeck et al. |
| 5,124,313 | A | 6/1992 | Schaeffer et al. |
| 5,202,826 | A | 4/1993 | McCarthy |
| 5,243,983 | A | 9/1993 | Tarr et al. |
| 5,275,168 | A | 1/1994 | Reintjes et al. |
| 5,290,605 | A | 3/1994 | Shapira |
| 5,303,026 | A | 4/1994 | Strobl et al. |
| 5,304,170 | A | 4/1994 | Green |
| 5,310,563 | A | 5/1994 | Curtis et al. |
| 5,346,488 | A | 9/1994 | Prince et al. |
| 5,348,018 | A | 9/1994 | Alfano et al. |
| 5,418,797 | A | 5/1995 | Bashkansky et al. |
| 5,421,337 | A | 6/1995 | Richards-Kortum et al. |
| 5,432,610 | A | 7/1995 | King et al. |
| 5,449,376 | A | 9/1995 | Callahan |
| 5,451,785 | A | 9/1995 | Faris |
| 5,452,723 | A | 9/1995 | Wu et al. |
| 5,537,314 | A | 7/1996 | Kanter |
| 5,552,997 | A | 9/1996 | Massart |
| 5,553,616 | A | 9/1996 | Ham et al. |
| 5,556,612 | A | 9/1996 | Anderson et al. |
| 5,567,628 | A | 10/1996 | Tarcha et al. |
| 5,579,773 | A | 12/1996 | Vo-Dinh et al. |
| 5,590,660 | A | 1/1997 | MacAulay et al. |
| 5,643,623 | A | 7/1997 | Schmitz et al. |
| 5,657,754 | A | 8/1997 | Rosencwaig |
| 5,666,223 | A | 9/1997 | Bennett et al. |
| 5,697,373 | A | 12/1997 | Richards-Kortum et al. |
| 5,730,714 | A | 3/1998 | Guy et al. |
| 5,733,507 | A | 3/1998 | Zakim |
| 5,734,838 | A | 3/1998 | Robinson et al. |
| 5,811,804 | A | 9/1998 | Van Blitterswijk et al. |
| 5,873,831 | A | 2/1999 | Bernstein et al. |
| 6,134,533 | A | 10/2000 | Shell |
| 6,205,354 | B1 | 3/2001 | Gellermann et al. |
| 6,408,281 | B1 | 6/2002 | Shell et al. |
| 6,415,265 | B1 | 7/2002 | Shell et al. |
| 6,421,648 | B1 | 7/2002 | Gagnon et al. |
| 6,595,929 | B2 | 7/2003 | Stivoric et al. |
| 6,621,574 | B1 | 9/2003 | Forney et al. |
| 6,690,966 | B1 | 2/2004 | Rava et al. |
| 7,039,452 | B2 | 5/2006 | McClane et al. |
| 7,088,233 | B2 | 8/2006 | Menard |
| 7,262,842 | B2 | 8/2007 | Ermantraut et al. |
| 7,365,839 | B2 | 4/2008 | Ferguson et al. |
| 2002/0022775 | A1 | 2/2002 | Finkelshteins |
| 2002/0072932 | A1 | 6/2002 | Swamy |
| 2002/0098588 | A1 | 7/2002 | Sammak et al. |
| 2002/0118361 | A1 | 8/2002 | Cadell et al. |
| 2002/0133080 | A1 | 9/2002 | Apruzzese et al. |
| 2003/0030798 | A1 | 2/2003 | Samsoondar et al. |
| 2003/0130579 | A1 | 7/2003 | McClane et al. |
| 2003/0148542 | A1 | 8/2003 | Pawlak et al. |
| 2004/0254479 | A1 | 12/2004 | Fralick et al. |
| 2005/0197580 | A1 | 9/2005 | Ferguson et al. |
| 2005/0197581 | A1 | 9/2005 | Ferguson et al. |
| 2005/0197582 | A1 | 9/2005 | Ferguson et al. |
| 2005/0278184 | A1 | 12/2005 | Fralick et al. |
| 2006/0092411 | A1 | 5/2006 | Ferguson et al. |

FOREIGN PATENT DOCUMENTS

| | | |
|---|---|---|
| EP | 0 607 941 | 7/1994 |
| EP | 0722692 A1 | 7/1996 |
| JP | 03-120445 | 5/1991 |
| JP | 10-153529 | 9/1998 |
| JP | 2002-286628 | 10/2002 |
| JP | 2003-507088 | 2/2003 |
| JP | 2003-108679 | 4/2003 |
| JP | 2003-530184 | 10/2003 |
| TW | 552126 B | 9/2003 |
| TW | 558635 B | 10/2003 |
| WO | 92/10131 | 6/1992 |
| WO | 92/15008 | 9/1992 |
| WO | 00/78217 | 12/2000 |
| WO | 01/78577 | 10/2001 |
| WO | 02/43585 | 6/2002 |
| WO | 02/063269 | 8/2002 |

OTHER PUBLICATIONS

Bays, R. et al. "Three-dimensional optical phantom and its application in photodynamic therapy," Lasers in Surgery and Medicine, Wiley-Liss, New York, US, vol. 21, No. 3, pp. 227-234 (Jan. 1, 1997).

Bell, S.E.J. et al. "Extracting Raman spectra from highly fluorescent samples with 'Scissors' (SSR, Shifted-Subtracted Raman Spectroscopy)," Raman Spectroscopy, Spectroscopy Europe 14/6, pp. 1-4 (2002).

Berendshot, Tos T. J. M., et al., "Influence of Lutein Supplementation on Macular Pigment, Assessed with Two Objective Techniques," IOVS, vol. 41, No. 11, pp. 3322-3326 (Oct. 2000).

Bone, R.A., Landrum, J.T., and Cains, A, "Optical Density Spectra of the Macular Pigment In Vivo and In Vitro," Vision Res., vol. 32, No. 1, pp. 105-110, 1992.

Brenan, C.J.H. et al. "Volumetric Raman microscopy through a turbid medium," Journal of Raman Spectroscopy, vol. 27, pp. 561-571 (1996).

Brody, J.E., "Health Factor in Vegetables Still Elusive," The New York Times, Section C, p. 1, (Feb. 21, 1995).

Cerussi, A.E. et al. "Chromophore detection by fluorescence spectroscopy in tissue-like phantoms," SPIE, 2979, pp. 139-150 (1997).

Dubois, D. et al. "Moldable tissue equivalent bolus for high-energy photon and electron therapy," Medical Physics, vol. 23, No. 9: pp. 1547-1549 (1996).

Elsner, Ann E., et al, "Foveal Cone Photopigment Distribution: Small Alterations Associated with Macular Pigment Distribution," IOVS, vol. 39, No. 12, pp. 2394-2404 (Nov. 1998).

Firbank and D.T. Delpy, M. "A design for a stable and reproducible phantom for use in near infra-red imaging and spectroscopy," Physics in Medicine and Biology, Taylor and Francis Ltd., London, GB, vol. 38, No. 6, pp. 847-853 (Jun. 1, 1993).

Firbank, Michael et al. "An improved design for a stable and reproducible phantom material for use in near-infrared spectroscopy and imaging," Physics in Medicine and Biology, Taylor and Francis Ltd., London, GB, vol. 40, No. 5, pp. 955-961 (Jan. 1, 1995).

Gellermann, W. et al. "Noninvasive laser Raman detection of carotenoid antioxidants in living human skin," SPIE, vol. 4244, pp. 36-44 (2001).

Gill, D. et al. "Resonance Raman Spectra of Conjated Polyvinylenes in Dichroic Polarizing Sheets (Polaroid KN-42)," Chemical Physics Letters, vol. 8, No. 6, pp. 634-636 (Mar. 15, 1971).

Gniadecka, Monika et al. "Distinctive Molecular Abnormalities in Benign and Malignant Skin Lesions: Studies by Raman Spectroscopy," Photochemistry and Photobiology, 66(4): 418-42 (1997).

Hammond, B.R., Fuld, K., and Curran-Celentano, J., "Macular Pigment Density in Monozygotic Twins," Invest. Ophthalmo. Vis. Sci., vol. 36, No. 12, pp. 2531-2541 (Nov. 1995).

Handelman, G.J., Snodderly, D.M., Krinsky, N.L., Russett, M.D., and Adler, A.J., "Bilogical Control of Primate Macular Pigment," Inv. Ophthalmol. Vis. Sci., vol. 32, No. 2, pp. 257-267 (Feb. 1991).

Hata, T. R. et al. "Non-invasive Raman spectroscopic detection fo carotenoids in human skin", Journal of Investigative Dermatology, vol. 115, No. 3, pp. 441-448 (2000).

Hunt, S. et al. "Spectroscopic characterization of low molecular weight fluids from silicone elastomers," Journal of Macromolecular Science, Pure and Applied Chemistry, vol. A39, No. 9, pp. 1007-1024 (2002).

Lambert, J. L. et al. "Measurement of aqueous glucose in a model anterior chamber using Raman spectroscopy", Journal of Raman Spectroscopy, vol. 33, pp. 524-529 (2002).

Land, Edwin H. "Some aspects of the development of sheet polarizers," Journal of the Optical Society of America, vol. 41, No. 12, pp. 957-963 (Dec. 1951).

Linear and Circular Polarizers, Vikniti Display Enhancement, 3M Corporation, pp. 1-8 (2001).

Lualdi, M. et al. "A phantom with tissue-like optical properties in the visible and near infrared for use in photomedicine", Lasers in Surgery and Medicine, vol. 28, pp. 237-243 (2001).

Makropoulou, M.I. et al. "Quantitative estimation of absorbing chromophores in tissue simulators based on laser induced spectroscopy and scattering measurements," SPIE vol. 4162, pp. 76-85 (2000).

Material Safety Data Sheet, Dow Corning® 3179 Dilatant Compound, pp. 1-6 (Jul. 7, 1997).

Pharmanex Biophotonic Scanner Operating manual, pp. 1-38 (Mar. 2003).

Pogue, B. W. et al. "Review of tissue simulating phantoms for optical spectroscopy, imaging, dosimetry," Journal of Biomedical Optics, SPIE, P.O. Box 10, Belingham, WA, 98227-0010, vol. 11, No. 4, pp. 41102 (Jul. 1, 2006).

Polyzois, G.L. et al. "Physical properties of a silicone prosthetic elastomer stored in simulated skin secretions," Journal of Prosthetic Dentistry, vol. 83, No. 5, pp. 572-577 (2000).

Schalch, Wolfgang, "Carotenoids in the Retina—A Review of Their Possible Role in Preventing or Limiting Damage Caused by Light and Oxygen," Free Radicals and Aging, Basel, Switzerland: Birkhauser Verlag, pp. 280-298 (1992).

Schut, Tom C. Bakker et al. "Intracellular Carotenoid Levels Measured by Raman Microspectroscopy: Comparison of Lymphocytes from Lung Cancer Patients and Healthy Individuals," Int. J. Cancer (Pred. Oncol): 74, 20-25 (1997).

Seddon, J.M., Ajani, U.A., Sperduto, R.D., Hiller, R., Blair, N., Burton, T.C., Farber, M.D., Gragoudas, E.S., Haller, Jr., Miller, D.T., Yannuzzi, L.A., and Willet, W., "Dietary Carotenoids, Vitamins A, C and E, and Advanced Age-Related Macular Degeneration," J. Am. Med. Assoc., vol. 272, No. 18, pp. 1413-1420, (Nov. 9, 1994).

Shim, M. G. et al. "Study of Fiber-Optic Probes for in vivo Medical Raman Spectroscopy", Applied Spectroscopy, vol. 53, No. 6, pp. 619-627 (1999).

Wagnieres, G. et al. "An optical phantom with tissue-like properties in the visible for use in PDT and fluorescence spectroscopy," Physics in Medicine and Biology, Taylor and Francis Ltd., London, GB, vol. 42, No. 7, pp. 1415-1426 (Jul. 1, 1997).

Wu, J. et al. "Three-dimensional imaging of objects embedded in turbid media with fluorescence and Raman spectroscopy," Applied Optics, vol. 34, No. 18, pp. 3425-3429 (1995).

Zhang, Qingguo et al. "Turbidity-free fluorescence spectroscopy of biological tissue," Optics Letters, vol. 25, No. 19, pp. 1451-1453 (Oct. 1, 2000).

BIO-PHOTONIC FEEDBACK CONTROL SOFTWARE AND DATABASE

RELATED APPLICATIONS

This application is a continuation of U.S. application Ser. No. 10/782,733 filed Feb. 19, 2004, which claims priority to U.S. provisional patent application Ser. No. 60/448,996 entitled SEAMLESS GLOBAL COMPENSATION SYSTEM filed Feb. 20, 2003, the contents of all of which are hereby incorporated in their entirety by reference.

BACKGROUND

1. The Field of the Invention

This invention relates to digital computers and photonic scanners, and more particularly, to unique apparatus and methods for timely, computerized, detection, tracking, and feedback control of the biological uptake of targeted nutrients.

2. The Background Art

The world of electronics and optical measurement systems is broad, varied, and has a long, colorful history. Systems for detection of optics by virtue of radar signatures, infrared signatures, and other spectral signatures have been used for decades. Accordingly, methods of detection and signal processing are plentiful.

In ancient times, nutrition and the art or science of the use of various herbs and naturally occurring compositions has been useful to the human race. In modern times, nutrition has received much public exposure as a science. The public is educated through schools, advertising, publications, government programs, and the like in order to improve nutritional habits. The field of pharmaceuticals, typically perceived to be either synthetic or processed drugs and medicaments has blended with nutritional sciences, and the art or science of herbal treatments and remedies. Nutriceuticals are products that fall in the area of nutritional and herbal materials that may provide additional remedial benefits.

Multi-level marketing has been a method of direct sale of products for many years. Multi-level marketing is built upon incentive programs whereby rewards are allocated to individuals and entities for the sale of product and the management of organizations. Typically, all proceeds derived from product sales are distributed according to an organizational genealogy relating various sales persons or dealers to managers and directors responsible for recruiting, training, motivating, supplying, and so forth, the front-line dealers. Compensation systems are themselves an art form of sorts. Moreover, management systems in organizations of all types have developed into various art forms, sciences, and the like, depending on one's view point and approach.

In the area of optics and detectors, U.S. Pat. No. 6,205,354 B1 issued Mar. 20, 2001 to Gellerman et. al. is directed to a method and apparatus for non-evasive measurement of carotenoids and related chemical substances and biological tissue. This patent is incorporated herein by reference. The method and apparatus of Gellerman et al. provide a non-invasive, rapid, accurate and safe determination of carotenoid levels, which, in turn, can provide diagnostic information regarding risk of disease or markers for conditions, such as carotenoids, or other antioxidant compounds. The method and apparatus utilize the technic of Resonance Raman Spectroscopy to measure the levels of carotenoids and similar substances in tissue.

In this technique, laser light is directed upon an area of tissue of interest. A small fraction of the scattered light is scattered inelastically, producing the carotenoid Raman signal, which is at a different frequency than the incident laser light. The Raman signal is collected, filtered, and measured. The resulting Raman signal can be analyzed such that the background fluorescent signal is subtracted and the results displayed and compared with known calibration standards.

Similarly, U.S. Pat. No. 5,873,831 issued Feb. 23, 1999 to Bernstein et. al. is directed to a method and system for measurement of macular carotenoid levels. This system, method, and apparatus provide for the determination of macular carotenoid levels. The invention measures the levels of macular carotenoid pigments, as well as other retinal materials. Monochromatic laser light is projected onto a retina, preferably in the macular area. A very sensitive detection system then takes the light scattered on the retina. Raman scattered light is selected and routed to a detection system, where the results are calibrated into actual standards for the particular retinal material being tested.

In the nutritional supplement area, much has been stated in technical, academic, trade, and consumer literature regarding antioxidants. Carotenoids are considered to be an antioxidant. Many herbs, foods, and processed compositions thereof provide antioxidants, including carotenoids.

In the area of multi-level marketing, U.S. Pat. No. 6,421,648 B1 issued Jul. 16, 2002 to Gagnon et. al. is directed to a data processing system for the management of a differential continuous compensation claim. This patent identifies a data processing system provided for monitoring and recording information flow and data, and making calculations necessary for maintaining a differential continuous compensation plan identified therein.

Likewise, U.S. Pat. No. 6,415,265 B1 issued Jul. 2, 2002 to Shell et. al., along with its sibling U.S. Pat. No. 6,408,281 B1 and parent U.S. Pat. No. 6,134,533 are directed to a multi-level marketing computer network server to integrate collection of a payment via the network and automatically distribute product with the calculation of commissions via the network.

U.S. Pat. No. 5,734,838 issued Mar. 31, 1998 to Robinson et. al. is directed to a database computing architecture for managing an incentive award program, and checking float of funds at the time of purchase. U.S. Pat. No. 5,537,314 issued Jul. 16, 1996 to Kanter is directed to a referral recognition system for an incentive award system. U.S. Pat. No. 5,202,826, issued Apr. 13, 1993 to McCarthy is directed to a centralized consumer cash accumulation system for multiple merchants, wherein credit value may be based upon predetermined incentives associated with a transaction such as coupons, rebates, discounts, credit rate, or a combination thereof.

Individuals often consult a doctor. The medical world is often reputed to be directed toward management by exception. That is, medical professionals are typically consulted for, and typically respond to, either acute or chronic symptoms of imbalance, trauma, stress, or ill condition. The nutritional science community is directed toward proper nutrition and maintenance of good health. Often, a non-medical health or nutrition inventory is simply not considered or done. It may be useful to a healthy individual to determine a status of antioxidants or carotenoid concentrations in the body.

Accordingly, it would be an advance in the art to provide a system for timely, non-medical diagnostic measurements of antioxidants, such as carotenoid content, as represented by the carotenoid content in skin. It would be a further advance in the art to couple this evaluation process with availability of nutritional supplements recognized for their antioxidant content, such as carotenoids.

It would be yet a further advance in the art to combine such a system with a marketing management and incentive system to compensate those who perform such inventories on healthy subjects, and those who market nutritional supplements associated with or directed to increasing amounts of targeted nutritional constituents (e.g., antioxidants, carotenoids, minerals, etc.), while managing the data relating the technological devices, the operators, the subjects, the consumers, and the marketing organizations.

BRIEF SUMMARY AND OBJECTS OF THE INVENTION

Accordingly, a method and apparatus in accordance with the present invention provide an integration of a technological device in accordance with the work of Gellerman, et al., applied to a process of inventory scanning of individuals for particular content of selected nutritional elements in the skin. One such nutritional element is the class of substances characterized as antioxidants and more particularly, a class of substances classified as carotenoids.

In certain embodiments, a system and method in accordance with the invention may provide computer code for communication between various computer systems. The system may include a laser illumination device and appropriate detection system, each including sufficient controller capacity for execution of their functions, and connected to other computational capacity to process the signals of the detector. Accordingly, such a system make take data, remove error, compensate for background noise, and ultimately fit the data to a curve or histogram providing an intensity value corresponding to a range of optical or other frequencies.

A computation system may be programmed to provide controls for the laser scanner and detection system, along with software to control the prompting and instruction of an operator, thus minimizing the skill level required of an operator. That is, much instrumentation is created strictly for the use of those highly skilled in the science to which it pertains. Moreover, much instrumentation is sufficiently complex, with only rudimentary controls, thus requiring a high level of skill and knowledge of both the science and the hardware in order to conduct operations. In a method and apparatus in accordance with the invention, a user interface programmed into a computer connected to a laser scanner may provide for simplified operation by a non-professional and non-technical operator.

Accordingly, the scanner takes data, provided to the master or host computer, and processes that data to determine the intensity of a Raman-Scattering response of the skin of a subject, as a result of laser illumination in a particular spectral band. The computer thus processes the data and provides a display to a user or operator regarding the content of the skin of a subject. For example, the carotenoid level may be identified directly, or identified in a relative sense as a score that may be compared with previous and subsequent scanning results.

The master computer may log data and upload it to a centrally based computer operated by an owner or affiliated company or other entity. For example, over a direct link or a world wide web link, the master computer may upload data regarding one or more scanning sessions to the central computer. Thus, many subjects over long periods of time may be tracked and recorded in a database.

Meanwhile, a system of method in accordance with the invention may provide for computer programs comprising executables and operational data for tracking and allocating compensation transfers between licensors of technology, operators of scanning devices used for taking inventory, sellers of nutritional supplements, and management organizations and individuals responsible for distributing nutritional supplements and motivating or training sales forces.

The central computing facility may track subjects, operators, sellers of nutritional supplements, organizational entities and individuals, managing, training, and distributing to supplement dealers, in order to allocate commissions for tasks performed thereby. Likewise, where technology such as a scanning device may be leased or licensed, royalties payable to owners of intellectual property may be calculated by a central computing facility. Likewise, systems may be programmed to allocate financial distributions to all entities involved. They may provide data for computers to actually apply credits or print checks, compensating individual entities having an association with the scanning process, the sales process, the manufacturing process, the distribution process, and so forth, associated with a cycle of scanning, and delivering supplements.

In one embodiment, a system and method in accordance with the invention may provide a scanner conducting multiple dozens of scans over some period of time. For example, in one embodiment, thirty scans of a subject may occur in approximately twenty seconds. Many data points may be collected. In one embodiment, 2,048 data points are collected with each scan for reading. Thus, thirty scans in approximately twenty seconds, each with 2,048 data points, may represent various pixels on a detector. That is, a detector may detect a light intensity for each of multiple frequencies received. In one embodiment, a charge-coupled device provides multiple pixels, each identified with a specific frequency, and each capable of integrating an intensity during a particular scan. Thus, the intensity of photons in a pixel identify the intensity at the subject frequency corresponding to the pixel.

Relying on Raman-Scattering, a frequency shift occurs between the input signal, illuminating the skin of a subject (consumer), resulting in an output back to a detector at a different end characteristic frequency. The curve fit of the overall detection spectrum can be processed to identify the intensity over the frequency range corresponding to carotenoid content of the user. In certain embodiments, noise may be calibrated out by comparing illuminations of neutral, opaque materials, and materials of known carotenoid content as well as unilluminated backgrounds in order to adjust the device field.

In certain embodiments, the scanner self-controls itself at some level of hardware. Typically, the hardware level is quite low, and the computational requirement is minimal for the self-control of a laser illumination source and a detector, such as a charged coupled device (CCD). A scanner containing a laser illumination source and a detector with the basic level of controls may connect to additional computation facility in another digital computer, such as a laptop, personal digital assistant, desktop computer, or the like. In the main computer or master computer to which the detector may connect, a dynamic link library may contain the processing applications required in order to take, process, log, and manage data. Meanwhile, other applications may connect through API (application programming interfaces) in order to access library routines, objects, or other executables.

Processing may include averaging multiple scan intensities, conducting dark scans to measure environmental noise, calibrating the reading of neutral background and a pre-determined level of detectable carotenoids in a calibration sample, compensating for temperature or other environmental factors, and the like.

The master computer may also include a user interface to provide prompting of a user (operator) in scanning a subject. Likewise, user interface may provide for prompts in database intake templates to obtain subject data, demographic information, environmental information, or any other data that may be useful either to the scanner or to the organization that may ultimately interact with the subject in marketing and tracking delivery of nutritional supplements. The user interface may provide a variety of processes for security, authorization, and other controls in order to ensure proper and authorized usage, reporting, and other compliance.

In one embodiment, a scanner may be operated by an operator who provides to a subject (consumer, visitor, customer, etc.) a result representing a score corresponding to antioxidant content such as carotenoid content in the skin of the subject. A consumer may pay to have a scan conducted. That is, individuals have their blood pressure checked at clinics, stores, and various other locations. Similarly, a consumer may go to a nutrition supplement store and have a carotenoid scan conducted.

In some embodiments of an apparatus and method in accordance with the invention, a purveyor of nutritional supplements may provide a certificate, such as a gift certificate, to a consumer or prospective customer, which certificate may be redeemed with any one of members of a network of people who operate scanners. Accordingly, the certificate, once redeemed, results in a certificate number or other identification corresponding to the operator and scanning machine that conducted the scan. Likewise, the certificate may have already been identified with the purveyor of nutritional supplements. By conducting intake questioning of the subject, the scanning operator can also link to the scan and certify the identification of the subject.

Subsequently, if and when a subject determines to purchase nutritional supplement products, a database system provided with the identification and information corresponding to the scanner, the operator, the certificate, and the subject may link a seller of product. Accordingly, a database system may contain enough information for processing of compensation systems for all parties and devices involved in the scanning, motivation, and delivery corresponding to the traditional supplements purchased by a customer.

Accordingly, each consumer (customer) may be tracked and further motivated by subsequent delivery of certificates valid for subsequent scanning in order to monitor skin carotenoid content in accordance with on-going ingestion of nutritional supplements directed thereto.

BRIEF DESCRIPTION OF THE DRAWINGS

The foregoing and other objects and features of the present invention will become more fully apparent from the following description, taken in conjunction with the accompanying drawings. Understanding that these drawings depict only typical embodiments in accordance with the invention and are, therefore, not to be considered limiting of its scope, the invention will be described with additional specificity and detail through use of the accompanying drawings in which.

DETAILED DESCRIPTION OF THE PREFERRED EMBODIMENTS

It will be readily understood that the components of the present, invention, as generally described and illustrated in the Figures herein, could be arranged and designed in a wide variety of different configurations. Thus, the following more detailed description of the embodiments of systems and methods in accordance with the present invention, as represented in FIGS. 1 through 13, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Many of the functional units described in this specification have been labeled as modules, executables, systems, servers, and the like in order to more particularly emphasize their implementation independence. For example, modules may be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module. For example, a module of executable code may be a single instruction, or many instructions, and may even be distributed over several different code segments, among different programs, and across several memory devices.

Modules may also be implemented in hardware as electronic circuits comprising custom VLSI circuitry, off-the-shelf semiconductors such as logic chips, transistors, or other discrete components. A module may also be implemented in programmable hardware devices such as field programmable gate arrays, programmable array logic, programmable logic devices or the like.

Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Figure 1:
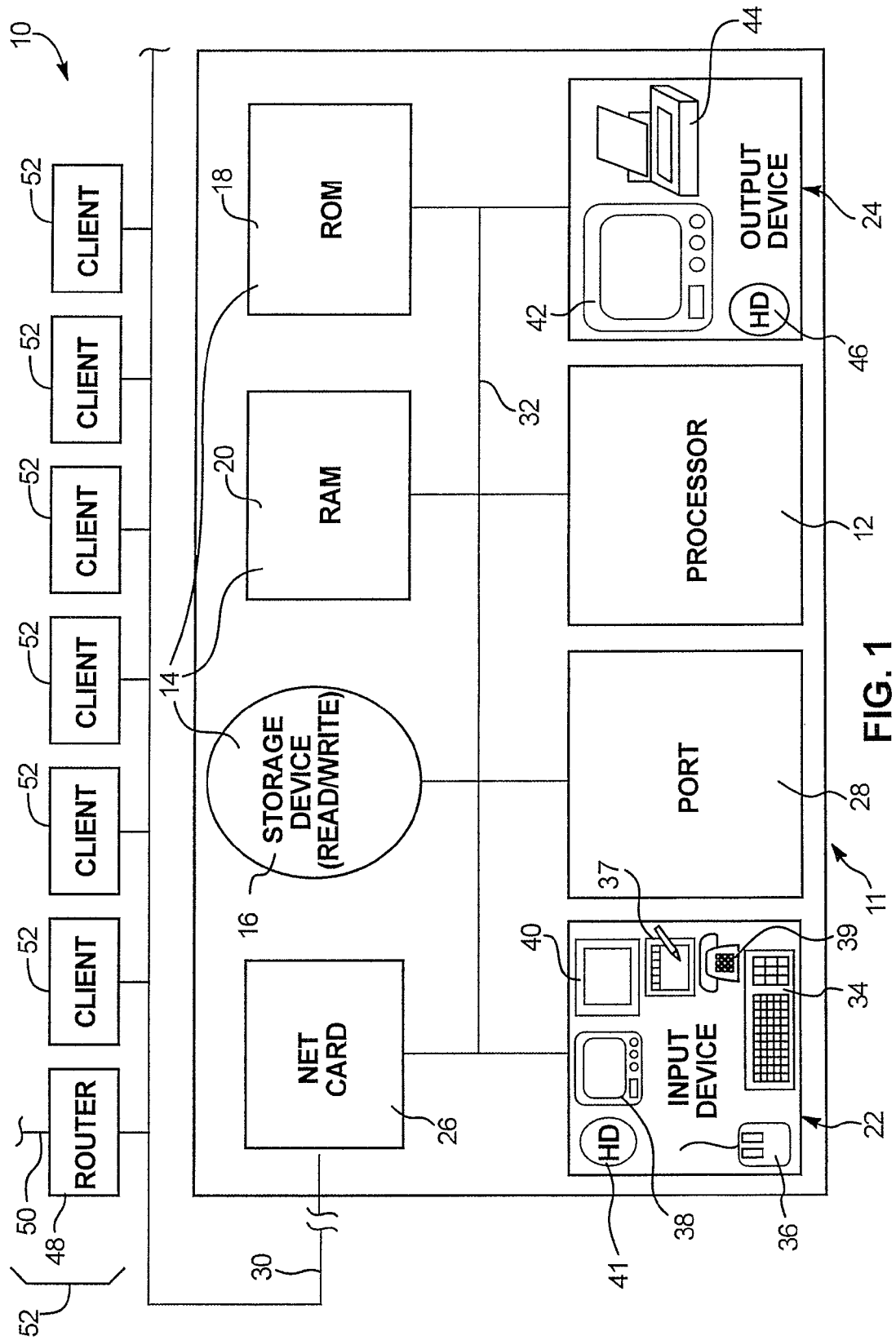
FIG. 1 is a schematic block diagram of a digital computer system such as may be used in various components in an apparatus and method in accordance with the present invention.

Referring to FIG. 1, an apparatus 10 may implement the invention on one or more nodes 11, (client 11, computer 11) containing a processor 12 (CPU 12). All components may exist in a single node 11 or may exist in multiple nodes 11, 52 remote from one another. The CPU 12 may be operably connected to a memory device 14. A memory device 14 may include one or more devices such as a hard drive or other non-volatile storage device 16, a read-only memory 18 (ROM 18) and a random access (and usually volatile) memory 20 (RAM 20 or operational memory 20).

The apparatus 10 may include an input device 22 for receiving inputs from a user or from another device. Similarly, an output device 24 may be provided within the node 11, or accessible within the apparatus 10. A network card 26 (interface card) or port 28 may be provided for connecting to outside devices, such as the network 30.

Internally, a bus 32, or plurality of buses 32, may operably interconnect the processor 12, memory devices 14, input devices 22, output devices 24, network card 26 and port 28. The bus 32 may be thought of as a data carrier. As such, the bus 32 may be embodied in numerous configurations. Wire, fiber optic line, wireless electromagnetic communications by visible light, infrared, and radio frequencies may likewise be implemented as appropriate for the bus 32 and the network 30.

Input devices 22 may include one or more physical embodiments. For example, a keyboard 34 may be used for interaction with the user, as may a mouse 36 or stylus pad 37. A touch screen 38, a telephone 39, or simply a telecommunications line 39, may be used for communication with other devices, with a user, or the like. Similarly, a scanner 40 may be used to receive graphical inputs, which may or may not be translated to other formats. The hard drive 41 or other memory device 41 may be used as an input device whether resident within the node 11 or some other node 52 (e.g. 52, 54, etc.) on the network 30, or from another network 50.

Output devices 24 may likewise include one or more physical hardware units. For example, in general, the port 28 may be used to accept inputs into and send outputs from the node 11. Nevertheless, a monitor 42 may provide outputs to a user for feedback during a process, or for assisting two-way communication between the processor 12 and a user. A printer 44, a hard drive 46, or other device may be used for outputting information as output devices 24.

In general, a network 30 to which a node 11 connects may, in turn, be connected through a router 48 to another network 50. In general, two nodes 11, 52 may be on a network 30, adjoining networks 30, 50, or may be separated by multiple routers 48 and multiple networks 50 as individual nodes 11, 52 on an internetwork. The individual nodes 52 (e.g. 11, 48, 52, 54) may have various communication capabilities.

In certain embodiments, a minimum of logical capability may be available in any node 52. Note that any of the individual nodes 11, 48, 52, 54 may be referred to, as may all together, as a node 11 or a node 52. Each may contain a processor 12 with more or less of the other components 14-46.

A network 30 may include one or more servers 54. Servers may be used to manage, store, communicate, transfer, access, update, and the like, any practical number of files, databases, or the like for other nodes 52 on a network 30. Typically, a server 54 may be accessed by all nodes 11, 52 on a network 30. Nevertheless, other special functions, including communications, applications, directory services, and the like, may be implemented by an individual server 54 or multiple servers 54.

In general, a node 11 may need to communicate over a network 30 with a server 54, a router 48, or nodes 52. Similarly, a node 11 may need to communicate over another network (50) in an internetwork connection with some remote node 52. Likewise, individual components 12-46 may need to communicate data with one another. A communication link may exist, in general, between any pair of devices.

Figure 2:
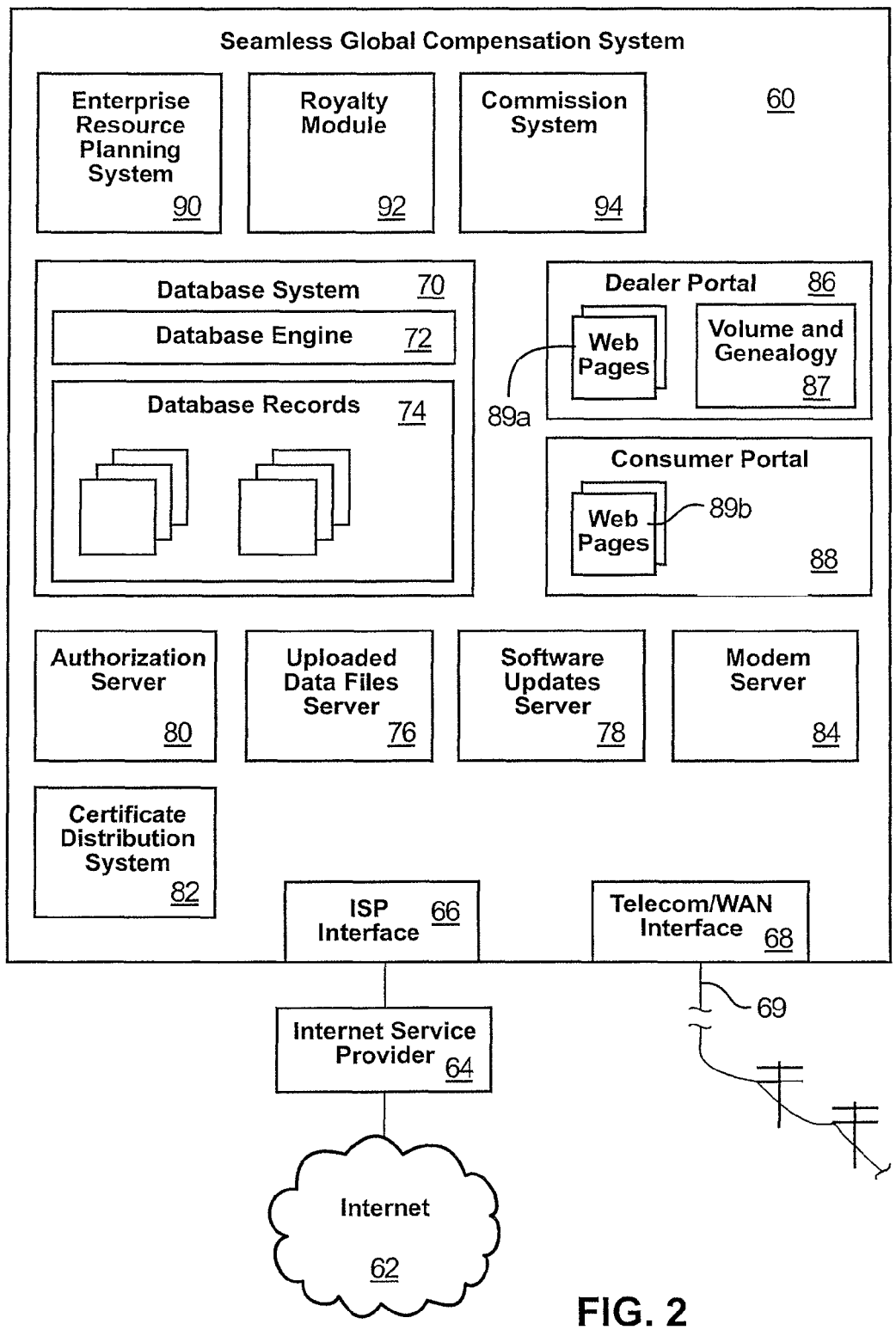
FIG. 2 is a schematic block diagram of a seamless, global, compensation system operable over a system of computers for managing a multi-level marketing system and a consumer scanning process.

Referring to FIG. 2, in one embodiment, a system 60 or a seamless, global compensation system 60 may include various elements of hardware and software in order to implement integration of marketing, tracking of management structures, tracking and execution of compensation, consumer testing and motivation, allocation and tracking of royalty payments, and delivery of nutritional supplements. In one embodiment, a system 60 may include hardware and software suitable to connect to the Internet 62. For example, an Internet service provider 64 may connect through an Internet service provider (ISP) interface 66 to the system 60. Alternatively, or in addition, a telecommunications interface 68 may connect to a conventional telecommunications network 69. In either event or both, the system 60 provides for communication with a network of customers, operators, dealers, managers, suppliers, and so forth.

In certain embodiments, the system 60 may rely on a database system 70. The database system 70 may be configured to operate in any of a host of modes. For example, object-oriented databases may embed both executables and attributes (operational data) into a single object associated with a particular function, purpose, entity or the like. Similarly, relational databases may operate by virtue of tables populated and managed by independent executables or database engines. Other applicable, logical constructs may be used instead.

Regardless of whether a database engine 72 is independent from database records 74 or embedded such that the database engine 72 and database records 74 are implemented with individual objects as executables and attributes, respectively, is not determinative. The database system 70 needs to provide the functionality of a database engine 72 capable of moving data in and out of database records 74 and providing for searching, indexing, and so forth of the database records 74 by whatever technological mechanism provides suitable functionality. Thus, the specific architecture of the database system 70 may be selected in order to provide desired functionality in view of available technology and the costs of creation and maintenance.

In certain embodiments, a server 76 may be programmed in software, hardware, or both to handle uploaded data files received from operators operating in accordance with the invention. For example, data files to be received for processing, or for inclusion directly into the database 74 may be uploaded from the Internet 62 or from a telecommunications network 69 from other users (customers, dealers, operators, etc.) into the server 76.

Software updates may be needed for interacting with the system 60 or for software for operating a scanner (see FIGS. 3-5, 10, scanner 102, for example). A server 78 may provide software updates to be downloaded to those in need, such as customers, operators especially, dealers or the like for whom software may be available. Typically, software updates may be provided by the server 78 to operators in order to provide the most recent operating characteristics for the scanner 102.

In certain presently contemplated embodiments, an authorization server 80 may manage and provide authorizations to operators, in order to properly conduct scans using the scanner 102. That is, for example, the intellectual property associated with the scanner is the subject of various patents, licenses, ownership, and the like. Accordingly, several mechanisms may be implemented in order to obtain financial returns on the efficacious use of a scanner 102. For example, if royalties are to be provided on the basis of use of a scanner 102, then the authorization server 80 may allocate, track, and otherwise control use, in order that royalties may be based upon use.

On the other hand, if machines are sold, then royalties may be paid based on the sale price of a scanner 102. Thus, an authorization server 80 may be tasked with responsibilities for allocating authorization on an ongoing or on a specific incident basis. Depending on the architecture selected, the servers 76, 78, 80 may all be connected to the database system 70. In an alternative embodiment, the data files server 76 may be connected to the database system 70 and may communicate with the authorization server 80 in order to properly perform the controlling functions thereof. Similarly, the software update server 78 may stand independently, or may be connected to other modules or elements of the system 60 in order to integrate the providing, tracking, and accounting for various services.

In certain embodiments, a certificate distribution system 82 may be configured in one of many ways. For example, the system 82 may actually be another server 82. In alternative embodiments, the system 82 may be a standalone hardware system. In certain embodiments, the certificate distribution system 82 may simply be embodied in certain executables that coordinate with or are incorporated within the authorization server 80. In other embodiments, a certain security process may be embodied to control a certificate distribution system 82 as a part of the database 70 itself.

In one presently contemplated embodiment, the certificate distribution system 82 may be embodied in the server or processor that connects to the server 76, in order that the server 76 may then interact with an operator to provide all of the necessary information, and collect all of the appropriate data with respect to the operator.

Similarly, the server 76 may connect to the authorization server 80, with the authorization server 80 providing the gate keeping function, and serving to an operator with the necessary authorization in exchange for the files to be uploaded to the server 76. Thus, a variety of connection and control schemes may be implemented in order to effect each of the functions of serving updated software to an operator, uploading files from an operator (or more properly from the computer thereof), serving authorizations to an operator and the computer of an operator, and distributing certificates for redemption by subjects who provide them to an operator in return for the scanning service.

In one presently contemplated environment, the server 80 may be regarded as the web server, and may receive information, provide authorizations, and forward to the database 70 from the server 76 the files uploaded to the server 76 by the computer 100 and operator. Nevertheless, regardless of the particular hardware and software that controls or executes the particular function, the database 70 may operate in accordance with an enterprise resource planning system 90. The planning system 90 may incorporate the software, data, or both that allocates, manages, tracks, and accounts for the resources of the enterprise served by the system 60.

For example, lease payments on hardware, commissions for sales, economic distributions to licensors owning property that is licensed, authorization of operation of scanners 102 within regions, geographical areas, market segments, and the like, and so forth, may all be considered resources. Likewise, financial streams are also resources. Accordingly, the enterprise resource planning system 90 may contain or create the plan, formula, or the control also for the allocation of resources in a system. Accordingly, the system 90 may provide to the database system 70 periodic updates of the plan incorporated therein.

Similarly, a royalty module 92 may be provided as an executable, system of objects, a server, or the like that provides for royalty controls and data with respect to licensed technology. For example, patented scanners 102 may derive royalties in accordance with the royalty schedule provided by, contained in, stored by, created by, enforced by, or delivered by the royalty module 92.

Similarly, a commission system 94 may contain, create, store, generate, allocate, control, deliver, or enforce a schedule of commissions, bonuses, and other financial or other remunerations to entities involved in the enterprise. For example, operators, in redeeming certificates, may obtain rights to financial compensation. Similarly, sales of product result in compensation to the sales people, managers, recruiters, and others who may be involved in the marketing enterprise. Thus, the enterprise resource planning system 90, the royalty module 92, and the commission system 94 provide the functionality to allocate financial and other resources among the entities that may be involved in the enterprise. Similarly, the authorization server 80, the certificate distribution system 82, as well as the uploaded data files server 76 and the software updates 78 handle the information data resources flowing into and out of the system 60.

In certain embodiments, a dealer portal 86 may include a volumes and genealogy module 87. The volumes and genealogy module 87 is responsible for publishing for the benefit of dealers, marketing products, as well as others who may have a need and right to know the allocations of the volumes of sales, however represented. Likewise, the genealogy portion of the volumes and genealogy module 87 provides the information regarding the relationships between networks of dealers, operators, and the like.

Accordingly, the genealogy of a multi-level marketing organization may be published for review of those who have responsibility or relationships with the organization and individuals. Similarly, the sales volumes of an individual dealer, or individual manager, and the portion of the network for which any individual or organization may have responsibility, may be made available in order that current, useful, appropriate information be made available for management and accounting purposes. In certain embodiments, the dealer portal 86 may be embodied in a web server as software, hardware, or both within the system 60. In certain embodiments, the entire system 60 may be hosted on a single computer, wherein each module or element is simply a programmed functionality, such as a software application.

The consumer portal 88 may likewise publish web pages 89 (e.g. 89*a*, 89*b*) for consumers. That is, the consumer portal 88 may allow a consumer to track purchases, scanning data from various inventories executed by a scanner 102, product information, dealer contact information, and so forth. A consumer portal 88 may be available to all consumers in general, specific consumers having authorization, or a combination thereof, as allocated by software, security, rights, and so forth.

In certain embodiments, a modem server 84 may provide a bank of modems for access by computers connecting through a telecommunications network 69. Accordingly, a modem server 84 may be operable within the system 60 through the telecommunication or wide area network interface 68.

Figure 3:
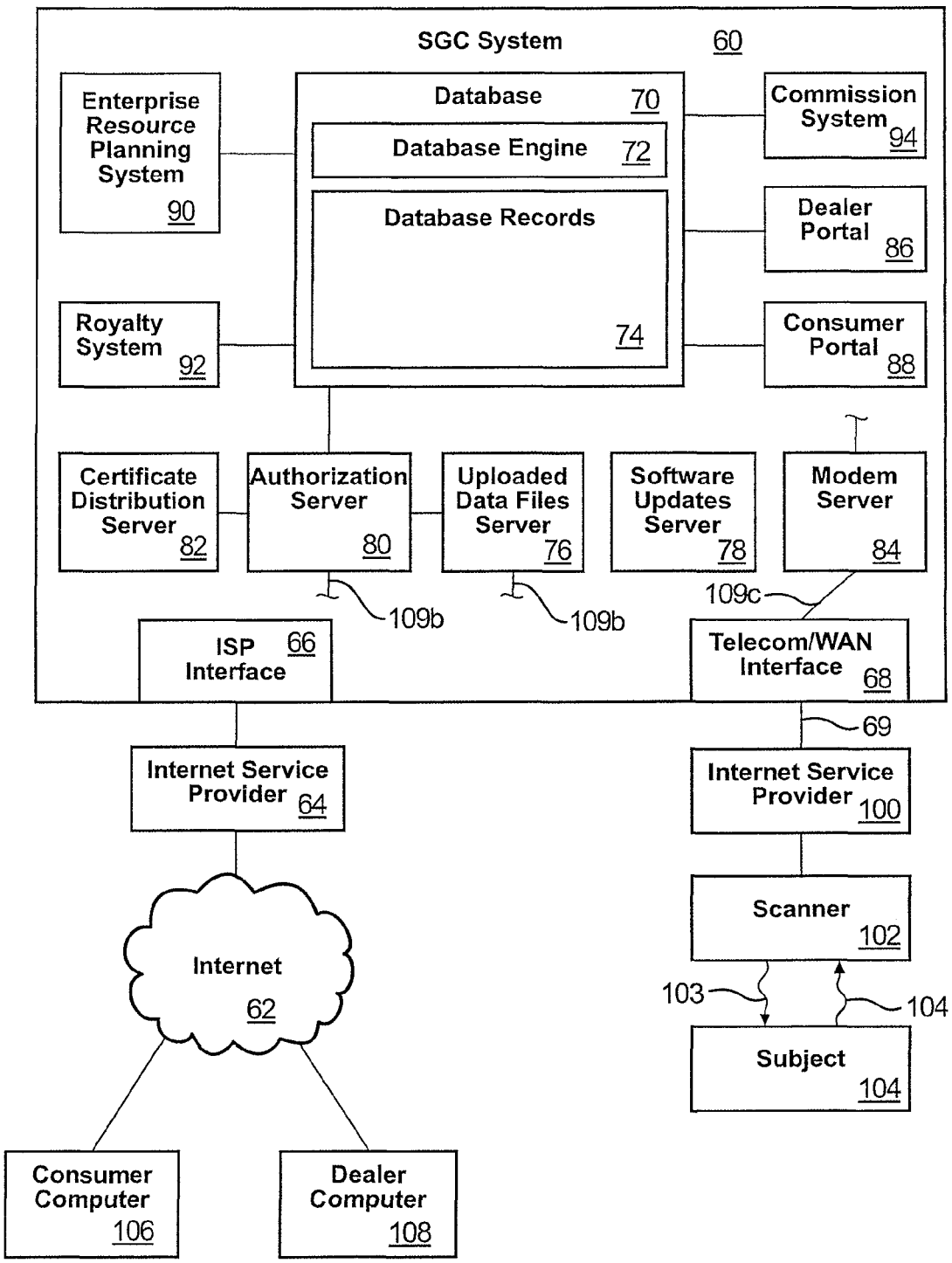
FIG. 3 is a schematic block diagram of an alternative embodiment of a seamless, global, compensation system operating both over the Internet and through direct connection to the system.

Referring to FIG. 3, one embodiment of the system 60 may include a user-interface host 100 connecting over a telecommunications network 69 to a telecommunications interface 68. In some embodiments, the interface 68 may be referred to as a wide area network (WAN) interface 68. Accordingly, the user interface 100 may be a computer, such as a desktop computer, a laptop computer, a personal digital assistant (PDA), or other processor. In certain presently contemplated embodiments, the user-interface 100 may be a portable, digital computer dedicated to the control and operation of the scanner 102.

The scanner 102 may be configured in accordance with the technology in U.S. Pat. No. 6,205,354 to Gellerman et. al. incorporated herein by reference. The scanner 102 directs a radiation beam 103 in a suitable spectrum onto a subject 104. A subject 104 may be, for example, the skin of a hand or arm of a prospective consumer. Due to Raman-Scattering, a shifted wavelength of light is returned from the input spectrum 103, as a beam 104. The beam 104 is accordingly detected by the scanner 102 and the data from the detector is processed accordingly, as discussed herein below.

In the illustrated embodiment of FIG. 3, a user-interface host 100 connects by a telecommunication interface 68 directly to the system 60. Thus, in this embodiment, the information provided by the scanner to the host 100 is received by the system 60 over a direct line, rather than over a less-secure Internet 62.

Meanwhile, a consumer computer 106 may connect to the Internet 62 in order to access from the system 60 the consumer portal 88. For example, the system 60 may engage through an Internet service provider 64 to publish web pages 89 over a consumer portal 88 on the Internet 62. These web pages 89 may be accessed by a consumer through the consumer's computer 106.

Similarly, a dealer computer 108 in possession of a dealer in nutritional supplements, for example, can connect to the Internet 62 in order to access a dealer portal 86. The dealer portal 86 may provide to the dealer computer 108 the volumes and genealogy programs 87 or the volumes of genealogy data 87 to which the dealer is entitled. Similarly, in the web pages 89 that the dealer should see may be published over the Internet 62 as part of the dealer portal 86 accessible to the dealer computer 108.

In the illustrated embodiment of FIG. 3, the system 60 may be configured with any connection scheme described with respect to FIG. 2. Nevertheless, for the sake of illustration, the illustration of FIG. 3 shows the database 70 as a "centerpiece" of the system 60, receiving and exchanging information with the enterprise resource planning system 90 and the royalty system 92. Similarly, the database exchanges information with the commission system 94 and the consumer portal 88. Intervening applications or connections may be implemented as appropriate.

In the illustrated embodiment, the dealer portal 86 may have access to the commission system 94 in order to publish to authorized dealers the information for which those dealers are authorized. Some methods of security may be implemented in a typical system 60 in order to provide secure access by only those entitled to receive it.

Similarly, the authorization server 80 may be connected over a line 109*a* to the telecommunication interface 68. Similarly, the uploaded data server 76 may be connected over a line 109*b* to the telecommunication interface 68. Thus, in the illustrated embodiment, representing one option, the authorization server 80 is connected to exchange information with the certificate distribution server 82 as well as with the uploaded data files server 76.

In this illustrated embodiment, the authorization server 80 connects to the database 70 and the certificate distribution server 82 and the uploaded data server 76, do not. Nevertheless, depending on the allocation of responsibilities between the database engine 72 and the authorization server 80, as well as the other servers 76, 78, 82, a suitable connection scheme and management scheme may be used to optimize the flow of data, the processing thereof, and the serving of appropriate information.

In the illustrated embodiment, the modem server 84 is directly connected by the line 109C to the telecommunication interface 68. In some embodiments, a modem server 84 may operate as a telecommunication interface 68, providing a bank of modems. Calls through multiple lines 69 offer access to a variety of user-interface hosts computers 100.

Figure 4:
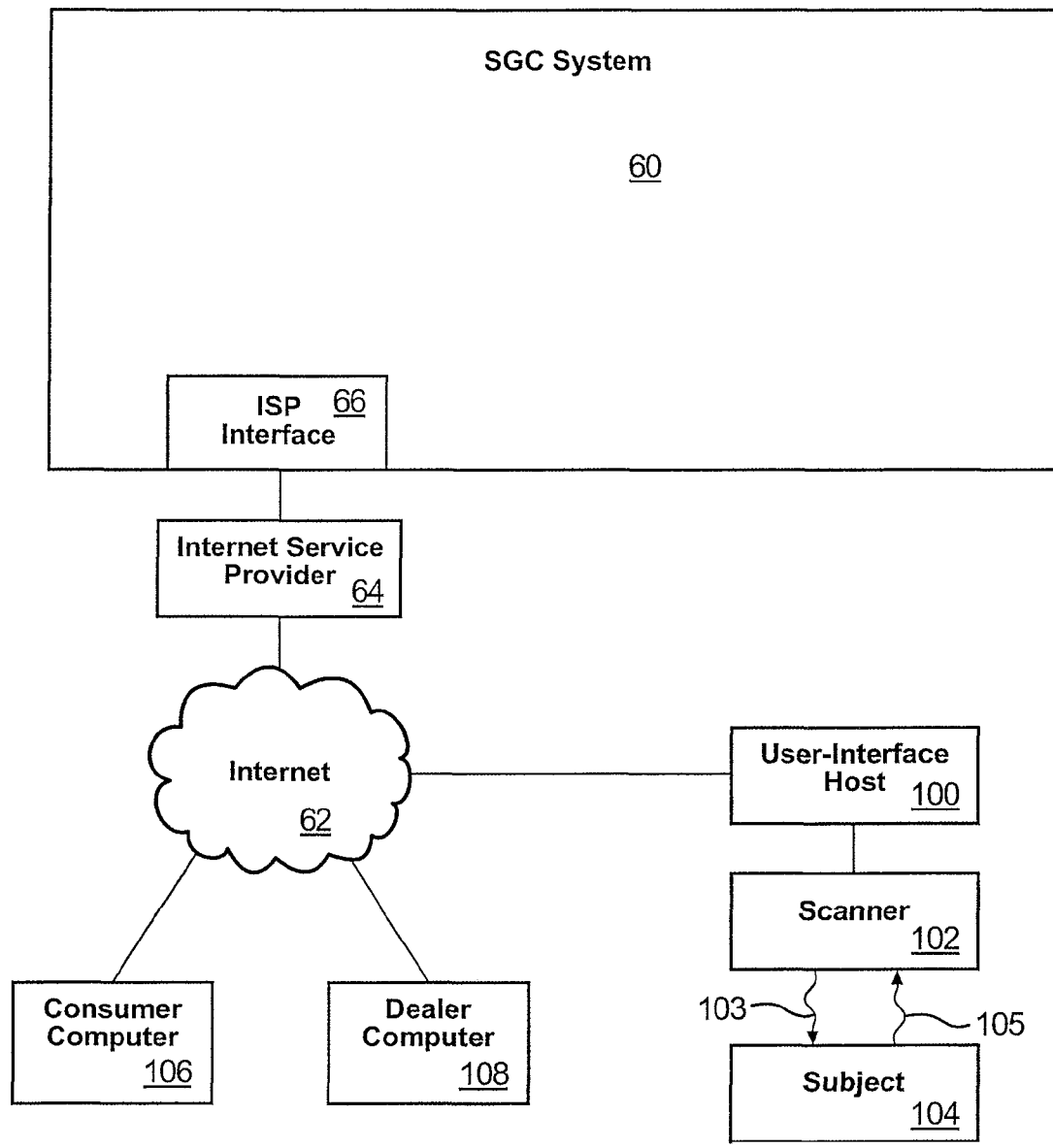
FIG. 4 is an alternative embodiment of a seamless, global, compensation system in accordance with the present invention, operable completely over Internet connections.

Referring to FIG. 4, in an alternative embodiment, the system 60 may connect strictly through the Internet 62. That is, consumer computers 106, and dealer computers 108 may access the Internet 62 in order to obtain access to the respective portals 88, 86 of the system 60. In yet another alternative embodiment, the consumer computer 106 and the dealer computer 108 may either one or both be connected through the telecommunication interface 68 to the system 60. However, with the ubiquitous presence of the Internet 62, along with the ability to cache web pages 89 locally, certain efficiencies accrue to publication of web pages 89 by the system 60 over the Internet 62 for the benefit of consumer computers 106 and dealer computers 108.

In the illustrated embodiment of FIG. 4, the user-interface host 100 connects to the system 60 through the Internet 62. In this embodiment, the system 60 may still host physically the information of the dealer portal 86 and the consumer portal 88 within the physical hardware at a central location of a system 60. The user-interface host 100 thus connects to deliver data from the scanner 102 to the system 60 through the Internet 62. In general, the user-interface host 100 may be a general purpose digital computer.

In other embodiments, the user-interface host 100 may be a special purpose computer. It may be programmed specifically to do only the functions allocated to it, and to be disabled from performing other functions. In this way, the host 100 may become a special purpose digital computer of limited capacity for purposes of security, control, license requirements, or the like.

Figure 5:
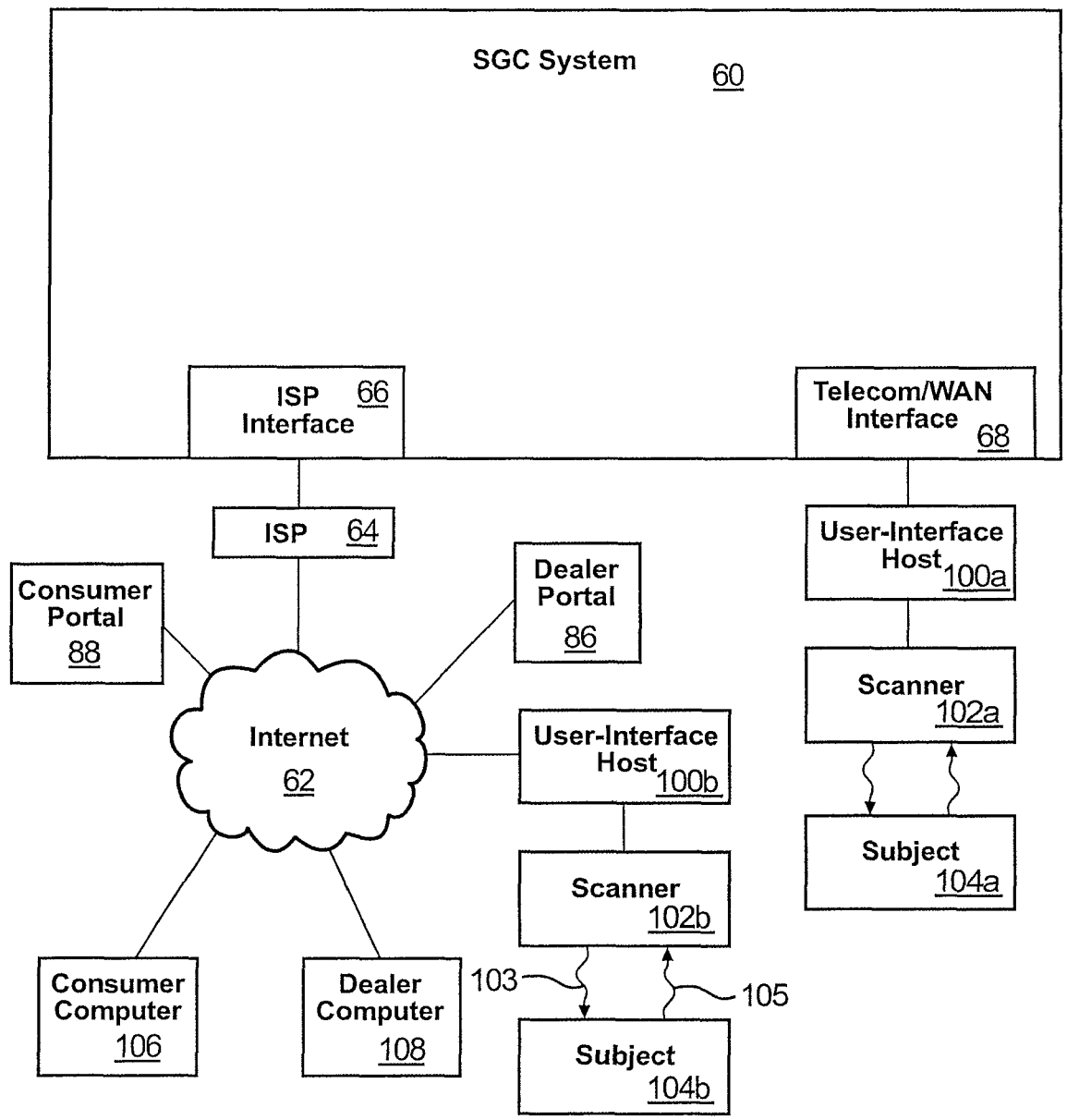
FIG. 5 is a schematic block diagram of an alternative embodiment of a seamless, global, compensation system in conjunction with a scanner system operable over the Internet and through direct connections.

Referring to FIG. 5, in yet another alternative embodiment, the system 60 may connect through a telecommunication interface 68 to one or more user-interface hosts 100*a*, supporting a scanner 102*a* for scanning a subject 104*a*. By the same token, the user-interface host 100*b* may connect through the Internet 62 and an ISP 64 in order to access the system 60. Many consider the Internet 62, absent appropriate measures, to be less secure than a direct line 69. Thus, in order obtain equivalent security, connecting through the Internet 62 may require additional software, signatures, and the like.

For simplicity, many prefer the direct dial system through a dedicated telecommunications line 69 to the telecommunication interface 68. Nevertheless, connecting through the Internet 62, as illustrated for the user-interface host 100b, is nevertheless a tractable option. In the illustrated embodiment, the consumer portal 88 and the dealer portal 86 may actually be connected to the Internet 62 at a location different from the majority of the hardware, software, or both of the system 60. In this embodiment, the dealer portal 86 and consumer portal 88 may actually be mere cache images published to local servers, in order to minimize the cost, complexity, time, and unreliability that may otherwise be encountered with global connections.

Thus, the dealer portal 86 and consumer portal 88 may actually be caches of identical or caches of a portion of another portal 86, 88 actually physically located within the system 60. Again, not illustrated here is the option wherein either the consumer computer 106, the dealer computer 108, or both connect through the telecommunication interface 68 in order to access the embedded dealer portal 86 or consumer portal 88 of the system 60, as illustrated in FIG. 3.

Figure 6:
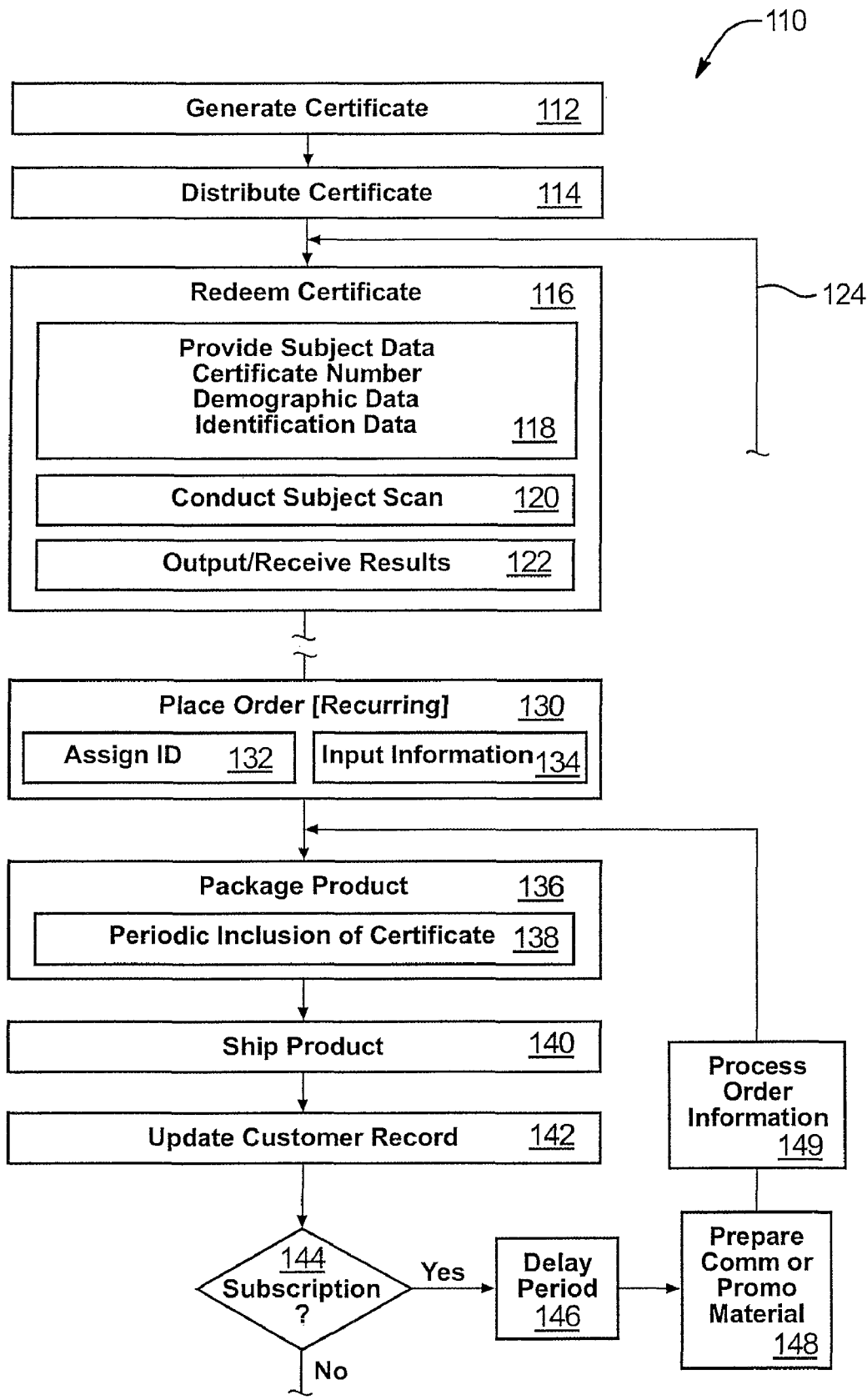
FIG. 6 is a schematic block diagram of a process for generating and redeeming certificates as a motivation for purchase of products related to conditions scanned in accordance with the invention.

Referring to FIG. 6, a process 110 for implementing certificates may provide a mechanism for compensation to dealers, operators of scanners 102, and others involved in the enterprise of taking inventories of the constitution of the skin of subject (potential consumers, consumers, etc.). The invention may provide motivation for the purchase of appropriate nutritional supplements. Sellers (dealers) of the supplements, the managers of dealers, the inventors of the scanner 102, and the suppliers of the nutritional supplements, and so forth may benefit by providing certifications. A certificate may be implemented in order to reallocate the cost of operating the scanner 102.

For example, a subject 104 may desire to have a scan conducted in order to determine the antioxidant or carotenoid content of one's skin. On the other hand, a dealer may be motivated to pay for the cost of a scan, in the hope of, or out of the proceeds of, a sale of nutritional supplements calculated to increase the antioxidant or carotenoid content of the subject's skin. Accordingly, a certificate may be purchased by a dealer. Likewise, certificates may be purchased by an operator of a scanner 102. Likewise, certificates may be produced by a manufacturer, supplier, or other purveyor of nutritional supplements as a motivation of the marketing chain.

Accordingly, a party having the resources and control, or simply the authorization or contractual opportunity to pay, an operator of a scanner 102, may generate 112 a certificate. According to any desired scheme, whether for direct cash payment, as a motivation for sales, as a reward, as a stimulant to re-purchase, as a reward for sales volumes, as a part of compensation, or otherwise, one may distribute 114 certificates to consumers, dealers, managers, operators, or the like.

In one embodiment, a supplier of nutritional supplements may generate 112 certificates. The generator (supplier) will compensate an operator of a scanner 102 according to the number of those certificates that are redeemed by the operator, and submitted back to the supplier. In another embodiment, an operator may purchase certificates as a mechanism for distribution 114. The operator may sell them directly to subjects 104, as a product in and of themselves.

Similarly, a dealer may purchase certificates in order to seed the market, knowing that some number of those certificates will result in scans that result in sales of nutritional supplements. Thus, by any and all appropriate methods, distribution 114 of certificates ultimately results in redeeming 116 those certificates.

When a certificate is redeemed 116, a subject 104 may provide 118 certain subject data relating thereto. For example, at the time of redemption 116, the certificate number may be provided. The certificate number allows for linking together a subject 104, and the scanner 102 or operator thereof that takes the scan, as well as the distribution 114 that obtained the certificate originally. Similarly, a subject 104 may provide demographic data that can be useful in targeting marketing, tracking trends, and observing the ultimate influence of nutritional supplements on populations and individuals. Likewise, identification data may be provided 118 by a subject 104 in order to positively identify a particular subject 104.

In certain embodiments, providing 118 subject data may be more or less intrusive. That is, the least intrusive collection might be some minimum amount of identification data associated with a certificate number. In other embodiments, long questionnaires with detailed data may be provided. In some embodiments, part of the purpose of motivation provided by a certificate may be the motivation to provide 118 the desired data. In other embodiments, the motivation to be provided by the certificate may reside more with an interest in one's personal score related antioxidant (e.g. carotenoid) to content of the skin.

Thus, at redemption 116, a scanner operator may conduct 120 a scan of a subject (person). After appropriate processing of the information by the host computer 100, an output 122 or receipt of results by a user provides a number. The number or score corresponds to the subject's carotenoid content in the skin. The output 122 may simply be a number to be compared with previous or subsequent scans of the same subject 104. In alternative embodiments, the output 122 may provide comparisons between a population at large, a world population, a comparative demographic population, or the like. Accordingly, the output 122 may provide motivation to a subject 104 to use nutritional supplements in order to effect the values of the output 122.

Ultimately, over a long or short period of time, the output 122 may result in a motivation to place 130 an order. Typically, and as shown in brackets as an option, placement 130 may be that of a recurring order. That is, a subject 104 may purchase a single order of product or may purchase a subscription for continuing delivery of product on a particular schedule.

Accordingly, upon placement 130 of an order for a delivery or a subscription for delivery of a product, the process 110 may assign 132 an identification to a user. Likewise, the system 110 or process 110 may obtain input 134 of information related to the subject 134. At this point, more information may reasonably be required, or expected, as the level of commitment to the results of the output 122 is exhibited.

In certain embodiments, the assignment 132 of an identification may include assignment of a user or consumer identification number. Similarly, dealers, operators, and the like may also have identification numbers that permit the database 70 to relate and track the activities of persons and organizations with respect to the operation of scanners 102 and the distribution of products.

In response to placement 130 of an order, packaging 136 of product consequently occurs, typically with a periodicity appropriate thereto. For example, a monthly shipment of product or a shipment keyed on a number of days, may correspond to the quantity of a daily supply of product provided.

As part of packaging 136, or possibly as an independent activity, inclusion 138 of a certificate may occur periodically.

For example, a certificate may be bundled in the packaging 136 of a product shipment to a consumer (subject 104). Likewise, product may be packaged 136 in one manner and the certificate inclusion 138 may actually be conducted by another. Certificates may move by mail, e-mail, facsimile, or the like. Thus, the periodicity of packaging 136 of a shipment, and the inclusion 138 or the distribution 138 of a certificate may be linked, may be synchronous, may be non-synchronous, but may actually be physically packaged 136 together.

Upon shipment 140 of a product to a customer, records may be updated 142 on a regular basis. Updating 142 may include records associated with not only the purchaser 104, but with the dealer involved, the management structure associated with the dealer, the originator of the certificate distributed 114, the scanner operator involved, and so forth.

If the placement 130 of an order can be by subscription, then the test 144 determines whether or not the order is to be repeated. If so, then after a delay period 146, preparation 148 of a communication or promotional material may occur. Ultimately, on schedule, processing 149 of order information results in packaging 136 of the next shipment. Again, inclusion 138 of an additional certificate may be on a corresponding schedule. For example, in one embodiment, every alternate shipment may receive inclusion 138 of a certificate. Thus, after two shipment cycles, a subject 104 may obtain a pre-test in order to verify that the nutritional supplements have indeed resulted in a different score as an output 122 of the scanning 120.

Optionally, preparation 148 of communications or promotional materials may be independent from a natural order. Thus, processing 149 of ordering information in certain embodiments may simply be processing of a proposed order in order to include it as a motivation to order. In any event, as certificates are made available, a return 124 to redemption 116 of the associated certificate may occur. The redemption 124 need not be in strict synchronization with the cycle of packaging 136 and shipping 140. That is, an order might not be a recurring order. Similarly, orders may have been cancelled. Likewise, the return 124 may be out of schedule, even if the shipment 140 or inclusion 138 of a certificate is on schedule. Moreover, a certificate may actually be given to a customer that does not have the need for a repeat of the scan 120 on schedule. Thus, in general, the return 124 may occur regularly as a result of motivation of an individual, and the availability of certificates, but may also take on a schedule of it's own, according to the convenience of a subject 104.

Figure 7:
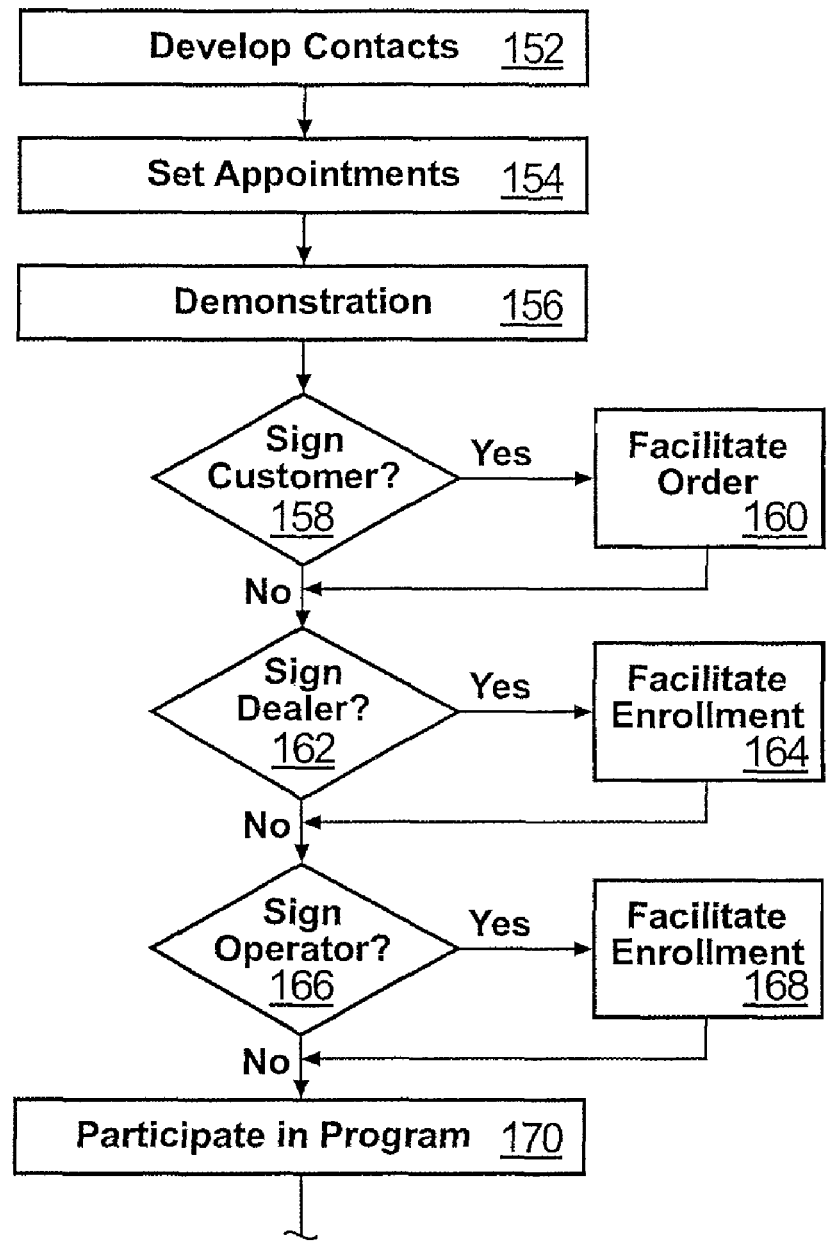
FIG. 7 is a schematic block diagram of a process for demonstrating a coordinated scanning system and a product system in order to scan for a condition addressed by the product.

Referring to FIG. 7, a process 150 for the development of a network of individuals in a multi-level marketing organization may begin with the development 152 of contacts who may be approached at some point. Accordingly, a dealer or manager in a marketing organization may set 154 appointments in advance or impromptu in order to conduct demonstrations 156. Demonstrations may occur in numerous areas. Likewise, a single demonstration may include different types of information in a single demonstration 156.

For example, in a method and apparatus in accordance with the invention, a demonstration 156 may include demonstration of an array of nutritional supplement products or the like. Likewise, a demonstration 156 may involve presentation of information related to the manufacturer, the marketing organization, the compensation system, or the like. Similarly, a demonstration 156 may include a demonstration of a scanner 102, along with the compensation system whereby an operator may operate a scanner 102 as a service. The service may be a standalone service, or may be provided in conjunction with sales of product.

Thus, as a result of a demonstration 156, various opportunities may be provided to attendees or participants in the demonstration 156. For example, a test 158 determines whether or not the demonstration 156 results in the sign up of a customer. If so, then a dealer may facilitate 160 the order. Since a method and apparatus in accordance with the invention may be embodied in various ways, facilitating 160 an order may involve assisting a customer to navigate the Internet, filling out an order form, logging on to a direct dial connection, or other mechanism for placing an order. Accordingly, a dealer may facilitate 160 the placement of an order by any suitable mechanism implemented over the Internet, by a direct dial connection, on paper, by telephone, or the like.

If the demonstration 156 results in signing a dealer, then the test 162 results in a dealer facilitating 164 enrollment on the new dealer. That is, a customer or consumer may be enrolled by facilitating 164 enrollment of that customer as a dealer by any of the mechanisms available. For example, paper, e-mail, Internet browser access, direct dial access, or the like, or some combination thereof, may be used for enrollment. Accordingly, one conducting a demonstration 156 may use any and all available methods as appropriate to facilitate 164 the enrollment of a new dealer.

If the demonstration 156 results in signing up an operator, the test 166 results in facilitating 168 enrollment of an operator. Facilitating 168 may involve a number of steps, including obtaining access to a scanner 102 in order to conduct scans. Similarly, with some degree of training, some degree of commitment, contracting, or the like, may be appropriate. Accordingly, over a direct line connection, the Internet, through paper, or the like, an individual demonstration 156 may facilitate 168 enrollment of an operator.

Consequently, participation 170 within a program, as a customer, as a dealer, as an operator, or any combination thereof, is contemplated. In any event, suppliers can provide product, sales materials, information, and devices, in order to participate 170 as a customer, dealer, operator, or combination thereof.

Figure 8:
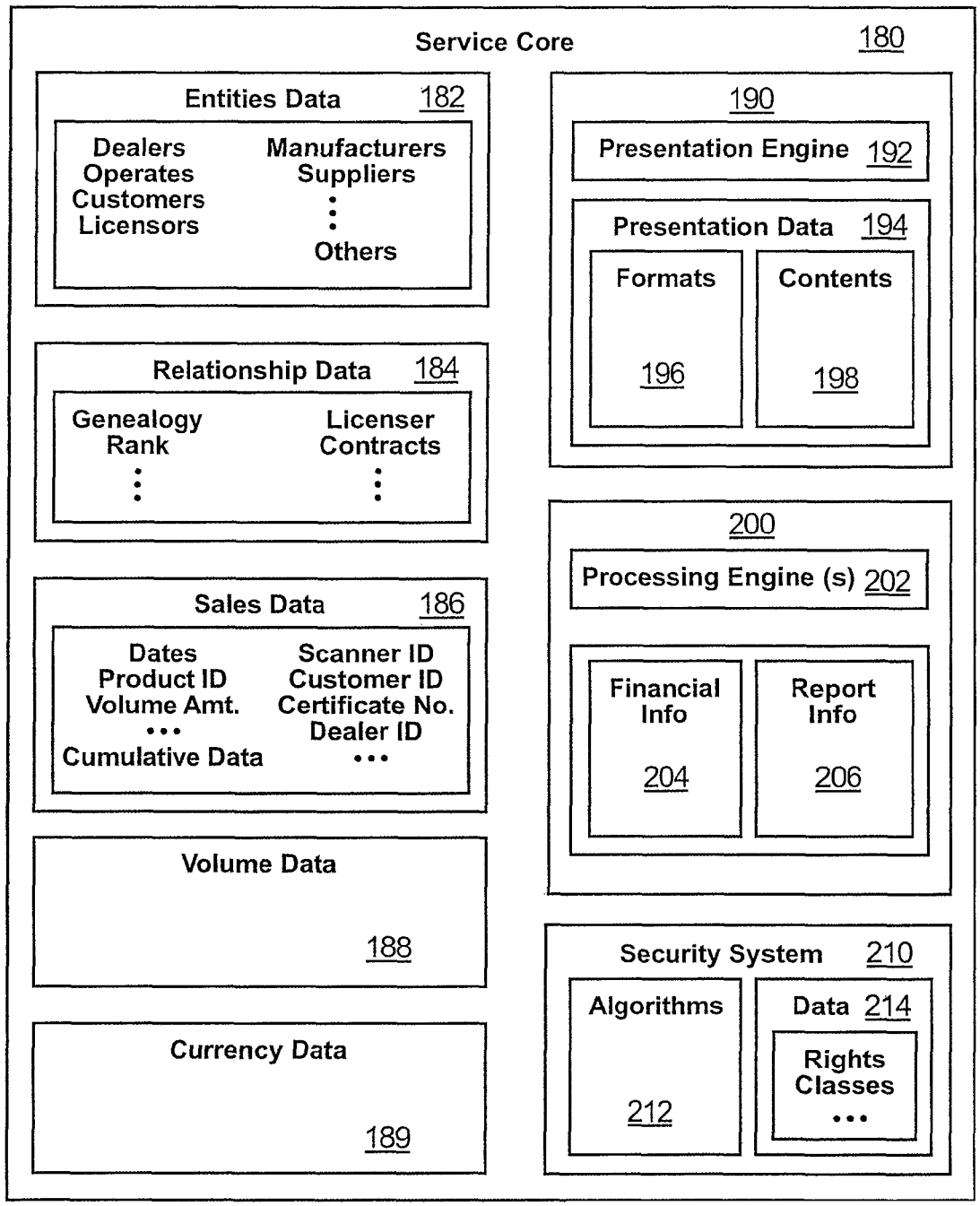
FIG. 8 is a schematic block diagram of a service core including data and executables for managing and presenting multi-level marketing information and associated scanning information.

Referring to FIG. 8, a method and apparatus in accordance with the invention may include a service core 180. In order to operate the system 60, entities data 182 may be maintained by the database 70. Entities data 182 may include information regarding dealers, operators, customers, licensors, manufacturers, suppliers, and others. Accordingly, identification information, locations, contact information, as well as other business information and financial information may prove useful or necessary to complete the data 182.

Relationship data 184 may be some of the most important. That is, dealers, customers, operators, and the like, often times operate together, or have various relationships that result in business connections, financial connections or the like. Accordingly, relationship data 184 may include genealogy (multi-level marketing relationship lines, etc., for example), rank (e.g., based on organizational size, depth, production volume, etc.) of an individual or entity on which compensation (for example) may be based. Licensure, including licensors and licensees, contracts, and other information may be included in relationship data 184. The relationship data 184 is particularly important for communication and for compensation.

Sales data 186 may include dates of events, such as presentations, sales, scans, and the like. Likewise, the data 186 may include product identification, volume amounts of particular products, a normalized volume amount that relates more to dollar volume, and cumulative data over various periods of interest in sales or other activity. Similarly, sales data 186 may include scanner identification, customer identification, certificate numbers, dealer identification, and other information that may assist in relating sales to entities 182 and relationships 184.

Likewise, volume data 188 may be thought of as any and all information that may be useful in determining sales performance of individuals and entities. Since relationship data 184 includes genealogy relationships between dealers in the organization, the volume data 188 associated with each of those individuals may depend on those relationships. For example, the commission for a sale directly to a consumer dealer may be a higher, typically, than a commission paid to that same dealer on the same sale.

Nevertheless, as volumes increase within a particular dealer or manager's organization, the rates of compensation for volumes may increase, as an incentive. Thus, the volume data 188 may be dated that operates as intermediate information from sales data 186 to identify key information that may be required for compensation schemes and schedules. Volume data 188 may be the inputs, outputs, or both for compensation equations. The volume data 188 may be raw data, or may be intermediate data incorporating both sales data 186 and relationship data 184, or may be a combination thereof.

Inasmuch as marketing is becoming a global enterprise, currency data 189 may be important. For example, in the service call 180, currency data 189 will be needed in order to provide compensation between individuals or other entities who have relationships defined by the relationship data 184 that span different countries. For example, Asia has several currencies. Similarly, Europe has had various currencies, although it is now trying to standardize on the Euro.

Nevertheless, it is not uncommon for individuals to have contacts across national boundaries and language boundaries, due to the availability of travel, and the communication of language. Thus, Latin American countries may have relationships spanning one or more countries. Similarly, dealers or others within the United States may have relationships with Europeans, Asians, Africans, Latin Americans, and so forth. Thus, the currency data 189 and the service call 180 provides for manipulation of compensation schemes in order to account for credits of payments in proper currencies.

The data 182, 184, 186, 188, 189 may be maintained in the database 70. Nevertheless, presentation systems 190 are typically required in order to provide presentation graphics, data, formatting thereof, and the like. Accordingly, a presentation engine 192 may be programmed to provide presentation data 194 to any visitor to a consumer portal 88 or a dealer portal 86. Similarly, any individual access to the system 60 for any reason, and by any mechanism, may need to have presentation of information.

Likewise, the user-interface host 100 requires a presentation engine 192 in order to interact with an operator. The presentation data 194 may be thought of as including formatting 196, and content 198. Typically, content 198 is often the subject of database storage. In other embodiments, formatting information 196 may also be included in the database 70. The sophistication of the database records 74 may be increased or decreased, according to exactly how much presentation data 194 and which types (e.g., formats 196, vs. content 198) will be included therein.

Likewise, processing systems 200 are important for handling information transfer. For example, a database engine 72 often contains very sophisticated programming in a number of different library or other executable programs in order to intake, output, and manage database records 74. Some of the requirements presently contemplated for a processing system 200 may include a processing engine 202 that is programmed to process information. Some of the information to be processed may include financial information 204 and report information 206.

For example, financial information 204 may include raw data, partially processed data, personal data, and the like for any individual consumer, dealer, organizational person, entity, or the like. Similarly, report information 206 may include information regarding sales volumes, current multi-level marketing network affiliations and individuals, and the like. Thus, the processing engine's operating on financial information 204, report information 206, or other information that should be presented to management, consumers, dealers, licensors, or the like, may be managed by various processing engines 202. Similarly, the financial information 204, or report information 206, may be raw data or finished data, and thus may be the same as database records 74, or processed further for output as content 198 by presentation engines 192.

Typically, Internet systems available widely benefit from a security system 210. Executables 212 or algorithms 212 implementing security may operate in accordance with data 214 such as passwords, rights, classifications or classes of entities and individuals, classes of information, and the like. Thus, a security system 210 may execute algorithms 212 in order to verify, obtain, or operate in accordance with data 214 on which a security system 210 depends.

Figure 9:
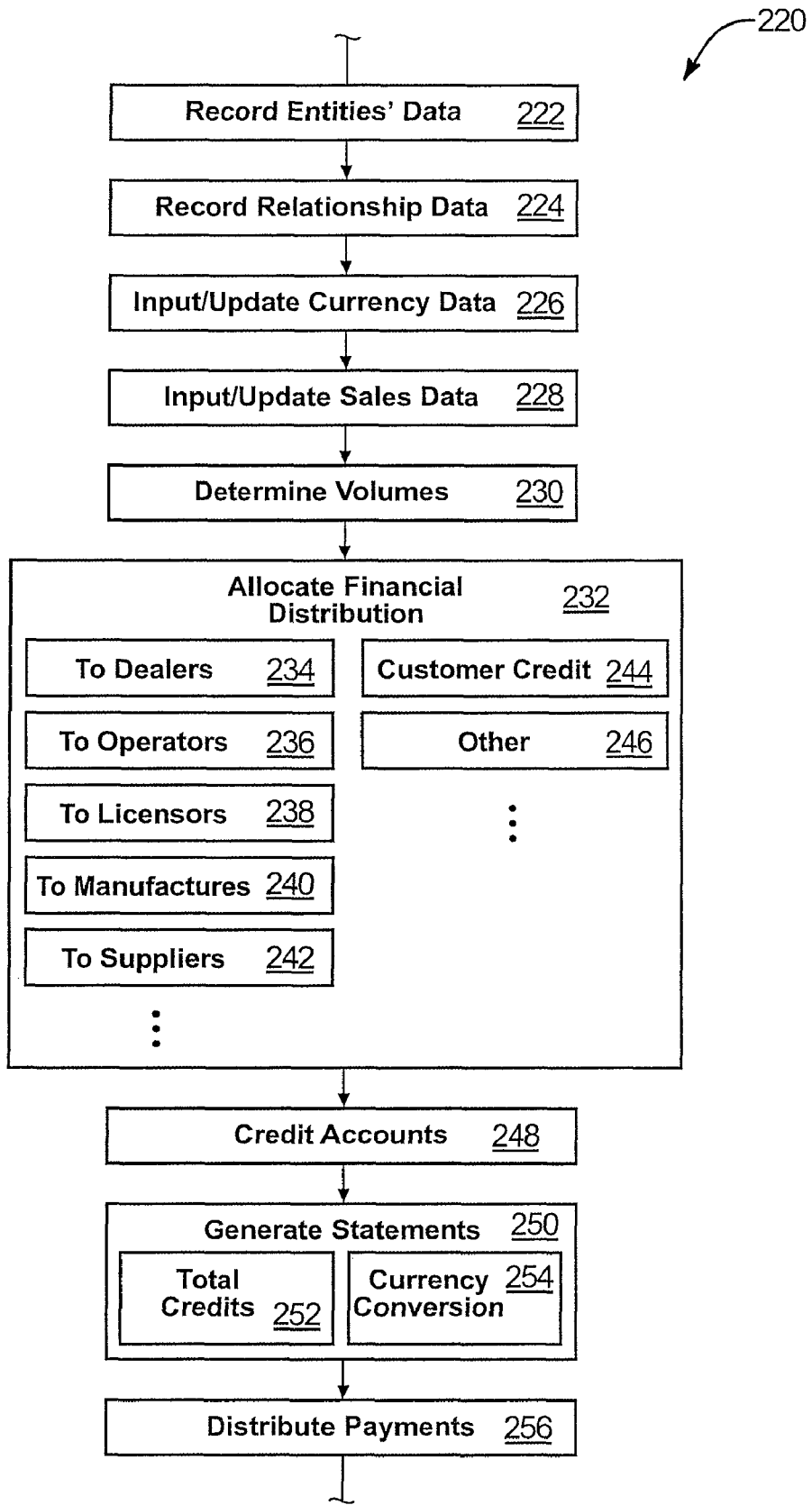
FIG. 9 is a schematic block diagram of one embodiment of a process in accordance with the invention for allocating financial distributions in accordance with a product, a scanning system, and a global network of relationships between individual entities.

Referring to FIG. 9, a process 220 for managing compensation may include recording 222 data corresponding to various entities. That is, whenever any dealer is enrolled, a customer places an order for product or a subscription for product, or when an operator is enrolled, data may be recorded 222 in order to identify, manage, support, and compensate that entity.

Likewise, recording 224 relationship data 184 may be conducted before or after the recording 222 of entity data. Nevertheless, since entities are typically known first, and relationships develop thereafter, relationship data 224 may be recorded 224 simultaneously or subsequent to the recording 222 of entity data 182.

Input 226 of currency data may include initial input 226 as well as updates 226 of currency data 189. Inputs 228, including subsequent updates 228 of sales data 186 may be input as necessary, and appropriate. Determining 230 volumes of sales by dealers and entities is a processing operation to calculate sales volumes that will determine compensation, based on an individual entity as identified in the entity data 182, other related entities, relationship data 184 relating the entities together, and the sales data 186 giving rise to the sales and subsequent compensation. Accordingly, determining 230 the volume data 188 sets the stage for allocating 232 financial distributions. Financial distributions may include payments 234 to dealers, allocations 236 to operators, allocations 238 to licensors, payments 240 to manufacturers, payments 242 to suppliers, and so forth. Similarly, credits 244 may be made to customers as a result of purchase volumes in some compensation systems. Similarly, all other distributions 246 may similarly be allocated 232 based on the available volumes 230.

Likewise, in certain embodiments, certain accounts may be credited 248, rather than making payments immediately. For example, allocating 232 may be thought of as the process of determining financial transfers in accordance with the determination 230 of the determination 230 of the volumes associated with various entities 182. At some point, accounts must be credited 248 in accordance with the allocations 232.

Therefore, ultimately, statements may be generated 250. Statements may be generated 250 on some periodic schedule, such as monthly. Accordingly, the total credits 252 and the currency conversion 254 may be selected as of the date of crediting 248, or the date of the generation 250 of the statement. Any suitable and equitable process, that can be managed in view of currency fluctuations, may be implemented in the timing and conversion of crediting 248, totaling 252 the credits, and conversion 254 of currencies.

Ultimately, distribution 256 of payments is hoped for by all of those laboring in the enterprise. Accordingly, distribution 256 may be by electronic, paper, or cash mechanisms, as well as others. For example, sometimes, distribution 256 may be taken in product, rather than cash. Thus, one may inventory credits in product, rather than taking pay-outs in cash. For example, product given away as a promotional item, thus does not show up except as an inventory flow. In a largely electronic system, distributing 256 of payments may actually occur by wire transfers between accounts. Online banking is being promoted by financial institutions to reduce paper, and to reduce the labor associated with processing paper. Accordingly, distribution 256 may be partially or entirely by financial credits to electronic accounts by financial institutions.

Figure 10:
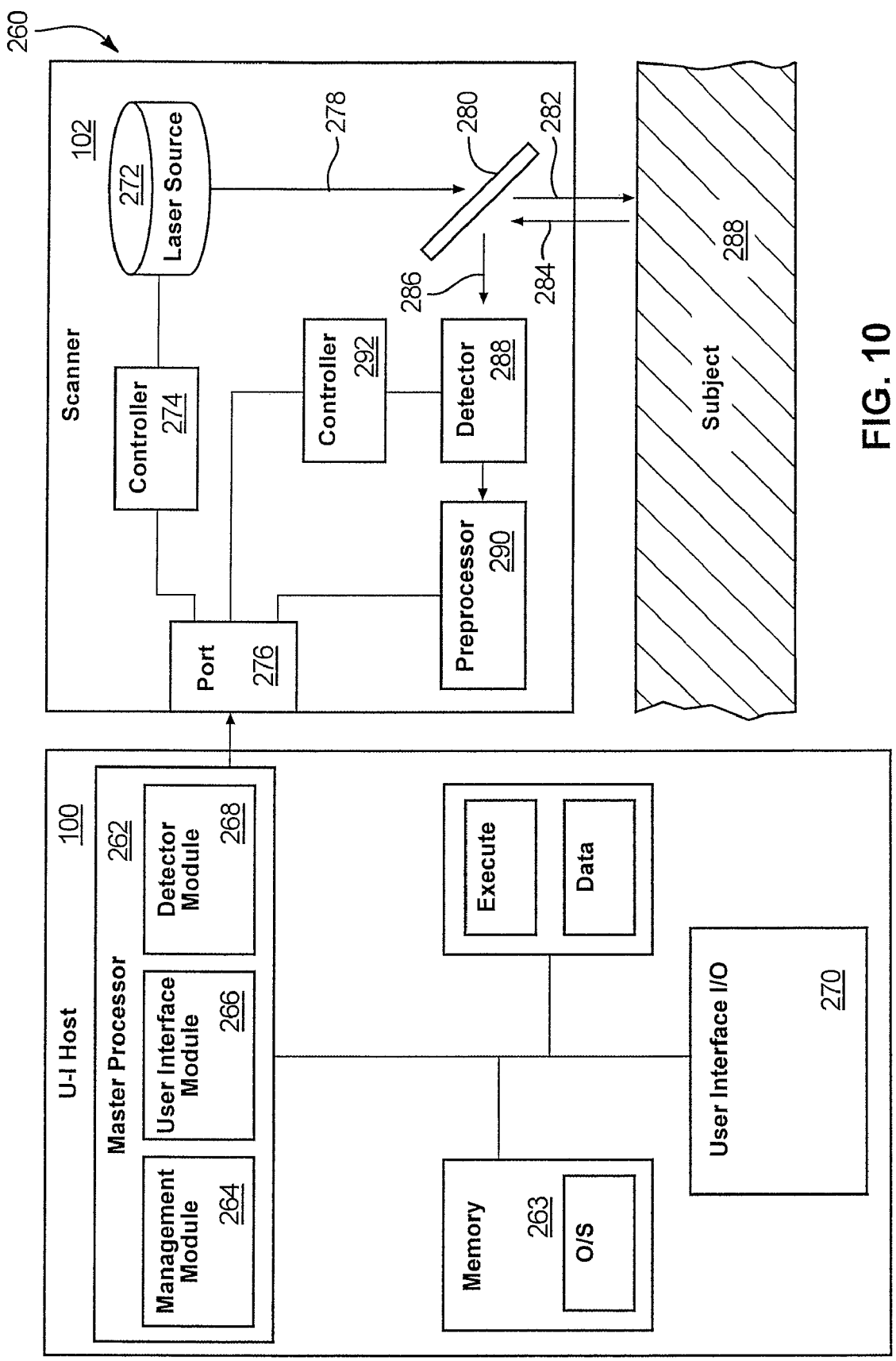
FIG. 10 is a schematic block diagram of one embodiment of a scanner and master processor that may operate as a scanning system and user-interface host in accordance with the invention.

Referring to FIG. 10, a user-interface host 100 or simply a host 100 may operate in conjunction with a scanner 102 as a system 260 for taking a survey or inventory of the hand, arm or other part of the skin of a subject 104. The subject 104 is typically a prospective consumer. The details of operation of the scanner 102 are disclosed by Gellerman (U.S. Pat. No. 6,205,354). A simplified schematic will suffice here. In general, a master processor 262 may be thought of as the CPU or processor within a host computer 100. Typically, the master processor 262 needs to accomplish several functions.

For example, a management module 264 may be programmed to execute on a processor 262 in order to manage the entire process. For example, a presentation 190 may be programmed to run on the processor 262 of the host 100. Similarly, a processing system 200 may be programmed into the processor 262 to handle various information. In the case of the host 100, financial information is of less consequence, and may be irrelevant.

That is, primarily technical information is processed from the scanner 102, and information available to a user is presented. Accordingly, a management module 264 may manage the order of presentation information, may include the control in order to process both the information received from the scanner 102, and the input and output information to a user (operator). Thus, in one embodiment, the management module 264 is responsible for any of the functionality and allocation of resources of the processor 262.

Meanwhile, a user interface module 266 provides the presentation graphics, the information, the prompts, and the intake and outflow of information required to step through the sequence of events in which the host 100 and scanner 102 operate together. Similarly, a detector module 268 may be allocated any or all of the processing of information coming from the scanner 102, as well as processing the information to be provided to the user interface module 266 as output.

The architecture of the master processor 262 as shown is in a very gross format. Numerous details are discussed later with respect to FIG. 13. Nevertheless, as a general proposition, the detector module 268 is responsible for data processing of information coming from the scanner 102. The user-interface module 266 is responsible for information presented to and retrieved from an operator. The management module 264 may control the operation of the processor 262, including control of the sequence of events conducted by the scanner 102. Thus, the management module 264 may be programmed to provide management of the interface between the user, the host 100, and the scanner 102.

A user-interface 270 may include any input and output systems reasonably required or helpful for an operator to interact with the host 100. For example, keyboards, a mouse, data input and output devices, drives, screens, printers, and the like, may all be used in suitable arrangement as input, output, or both devices for interacting with an operator.

In general, a scanner 102 includes a laser source 272, which may be provided by any suitable means. For example, lasers may be large or small. Light emitting diodes can produce laser light. A laser source 272 may have some degree of control embedded in it or connected with it by way of a controller 274 or controller 100. Nevertheless, typically, a laser source 272 may have some degree of local low level physical control embodied in a controller 274 directly associated or embedded therewith. Other hardware in the scanner 102 or the host 100 may provide additional instructions at a higher level to control the controller 274.

Eventually, the laser source 272 is controlled by signals received through a port 276 connecting the host 100 to the scanner 102. The module 264 may handle inputs, outputs, or both of the controller 274. Meanwhile, the laser source 272 projects a beam 278 to a director 280. The director 280 may or may not be necessary in various embodiments. In several embodiments, a splitter mirror may operate as a director 280 in order to pass the beam 278 through to become a beam 282 impinging on a subject 184.

As a result of the beam 282 striking the subject 184, a re-radiated or scattering beam (e.g. according to Raman scattering principles) returns as a beam 284 redirected by the director 280. The director 280 directs the beam 284 to become a beam 286 impinging on a director 288. Many intervening pathways, splitters, directors, filters, polarizing elements, and the like, may be implemented to meet the optical requirements of the beams 278, 282, 284, 286, any derivatives thereof, or contributions thereto. Again, the Gellerman patent provides additional details of various embodiments for implementing a scanner 102.

Ultimately, a beam 286 impinges on a detector 288 providing a representation or signal output corresponding to intensities and frequencies of energy contained in the beam 286. As with the controller 274 on the laser source 272, the detector 288 typically will have some low level hardware controller 292 connected thereto in order to facilitate communication with other hardware within the scanner 102, the host 100, or both.

The detector 288 provides a signal 289 that may pass through a pre-processor 290. That is, depending on the sophistication desired to be programmed into hardware, firmware, or software within the scanner 102 proper, a pre-processor 290 may execute analysis of the information that is output as raw electrical signals 289 from the detector 288. Typically, a pre-processor 290 may include functions such as sampling, smoothing, filtering, and the like. Information from a pre-processor 290 is ultimately passed to the host 100, and specifically to the detector module 268. The detector module 268 is responsible for processing data originating with the detector 288. Again, the schematic of the system 260 of FIG. 10 is for logical and gross representation of the functionality. Many separate components in multitudinous arrangements can be used to implement the functional requirements of the system 260 in order to provide a reading. That reading or output may be characterized as a body defense score (BDS) corresponding to the carotenoid content in the subject 104.

In general, the device of Gellerman is directed toward detection of carotenoids in the skin. Nevertheless, other systems 260 may scan different parts of subjects 104, including other tissues, and the like. Thus, although one embodiment of an apparatus and method in accordance with the invention would include a licensure of the Gellerman technology for implementation in the system 260 as the scanner 102, other technologies may also be applied in other embodiments.

Figure 11:
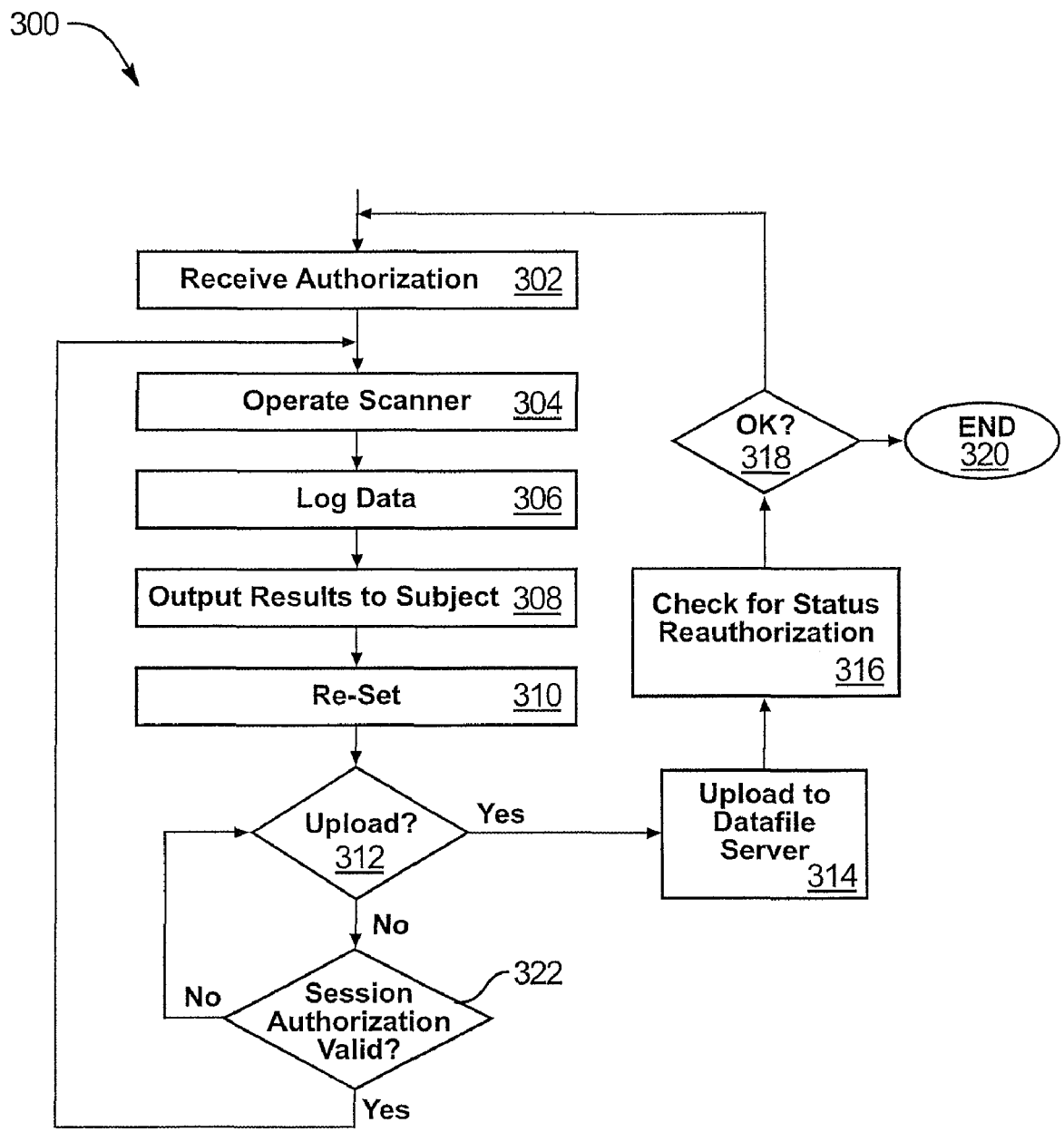
FIG. 11 is a schematic block diagram of a process for controlling authorization and operation of a scanner in accordance with the invention.

Referring to FIG. 11, a process 300 may control the scanner 102 and host 100 from a business perspective. For example, as discussed hereinabove, the system 60 may assert control over authorization received 302 in order to facilitate operation of the host 100 and scanner 102. In certain embodiments, the host 100 may be a dedicated computer. That is, it may be programmed with only a sufficient operating system and software to operate the scanner 102, and to interface with the operator and with the system 60. The host may have limited software by way of a connection to the Internet 62 or a telecommunication interface 68.

After receiving 302 authorization, an operator may operate 304 the scanner 102. The scanner 102, in the process of generating information to pass through the port 276 to the host 100, may receive subsequent programming, control, and the like. Meanwhile, the host 100 will log 306 all data in an appropriate order. That is, depending on the pre-processor 290, raw data may be logged. Processed data may also be logged.

Similarly, data may be logged from user information, subject information, and so forth. Ultimately, in the process of operating a scanner 102 and processing the information provided thereby, the host 100 will output 308 results of value to the subject. The results may be described graphically, in text, symbols, and the like. In one embodiment, the output 308 may occur by way of a graph.

In an alternative embodiment, that may be used in associated with such a graph, or independently, or instead of a graph, a number called a body defense score (BDS) may be output for a subject (potential customer, customer) to use for comparison with subsequent and previous BDS outputs received. In certain embodiments, a BDS of an individual may be compared to a BDS of a particular population in general, a world population, or a comparison standard of some particular type.

Data and machinery are most reliable and best for comparison when used under virtually identical circumstances with a minimum of changes in operating variables. That is, in general, a BDS output for an individual is best compared with a subsequent or previous BDS output from the same machine, rather than changing times, persons, machines, conditions all at once, and the like. Typical engineering principles recommend minimizing the number of altered conditions. Nevertheless, as data is collected and processed, more comparisons and more meaningful comparisons may be made. However, as a motivation for a subject 104 to participate in purchasing and ingesting nutritional supplements, a subject 104 need only receive an output 308 of a BDS number corresponding to relative amounts of carotenoids detected in the tissues (e.g., skin of the user). Lest false negative correlations or data result, however, machines should be reliably and repeatably operable and so calibrated.

A reset step 310 may involve simply setting up the host 100 to run a scan for another individual, or may involve shutting off the machine between multiple days or other periods of operation. A test 312 may determine whether or not a user (operator) desires to upload data that has been logged 306 during a previous particular time period or session. Sessions may be timed, numbered, or the like. That is, a session may be defined as a certain number of scans. Similarly, a session may be defined as a period of time during which the host 100 and scanner 102 are programmed to operate.

Ultimately, much or all data logged 306 is logged 306 with the intent to be uploaded. Accordingly, if the machine 260, or the operator determines to upload 314 data to the file server 109, the system 60 may on its own or through the host 100 check 316 for the status of regarding authorization. If authorization is okay, the test 318 results in a return to operation 304. Since authorization has been received, renewed, or otherwise activated.

If, on the other hand, the check 316 results in a revocation of authorization, or detects that an authorization time or number has been exceeded, then the test 318 may result in an end 320 to a session. The end 320 may result in the end of all operation of the scanner 102, host 100, or both.

One purpose for continuing checks 316 of authorization is that use is a proper licensing measurement for a patented invention. The scanner 102 may be sold, but also may be used, with throughput as a licensing measurement (metric). Accordingly, authorization can be checked 316 in order to verify that a machine 102 is being operated within its licensing authority. If the test 312, whether done manually, mentally, by virtue of programming within the host 100 results in no upload 314, then session authorization must still continue to be valid or operation ceases. If the session authorization is not valid, then a test 322 will typically permit only upload 314 operations. That is, if a user has not determined to reauthorize timely, or a corresponding prompt has been denied, then the test 312 may result in only one option, uploading 314, since the authorization tests out as invalid in the test 322.

Similarly, the check 316 for the status regarding re-authorization may include reporting back to the system 60 in order to verify the authorization status, whether new authorizations need to be granted, and the like. Ultimately, the process 300 results in several valuable functions. Examples are logging 306 data, outputting 308 results to a subject to provide motivation and progress reporting, uploading 314 data to the system 60 from the host 100, and testing 322 for authorization provide control by the system 60 of the remote operation of the scanner 102 and host 100.

However, implementation details may vary widely. Sequences of events may vary widely. Whether a single machine, multiple machines, a single software package, multiple software packages, a single machine instruction, or a massive multi-media package are involved, the illustrated logical functionality of the system may accomplish the valuable functions with the desired minimum or maximum fanfare, splash, ease, presentation graphics, and so forth.

Figure 12:
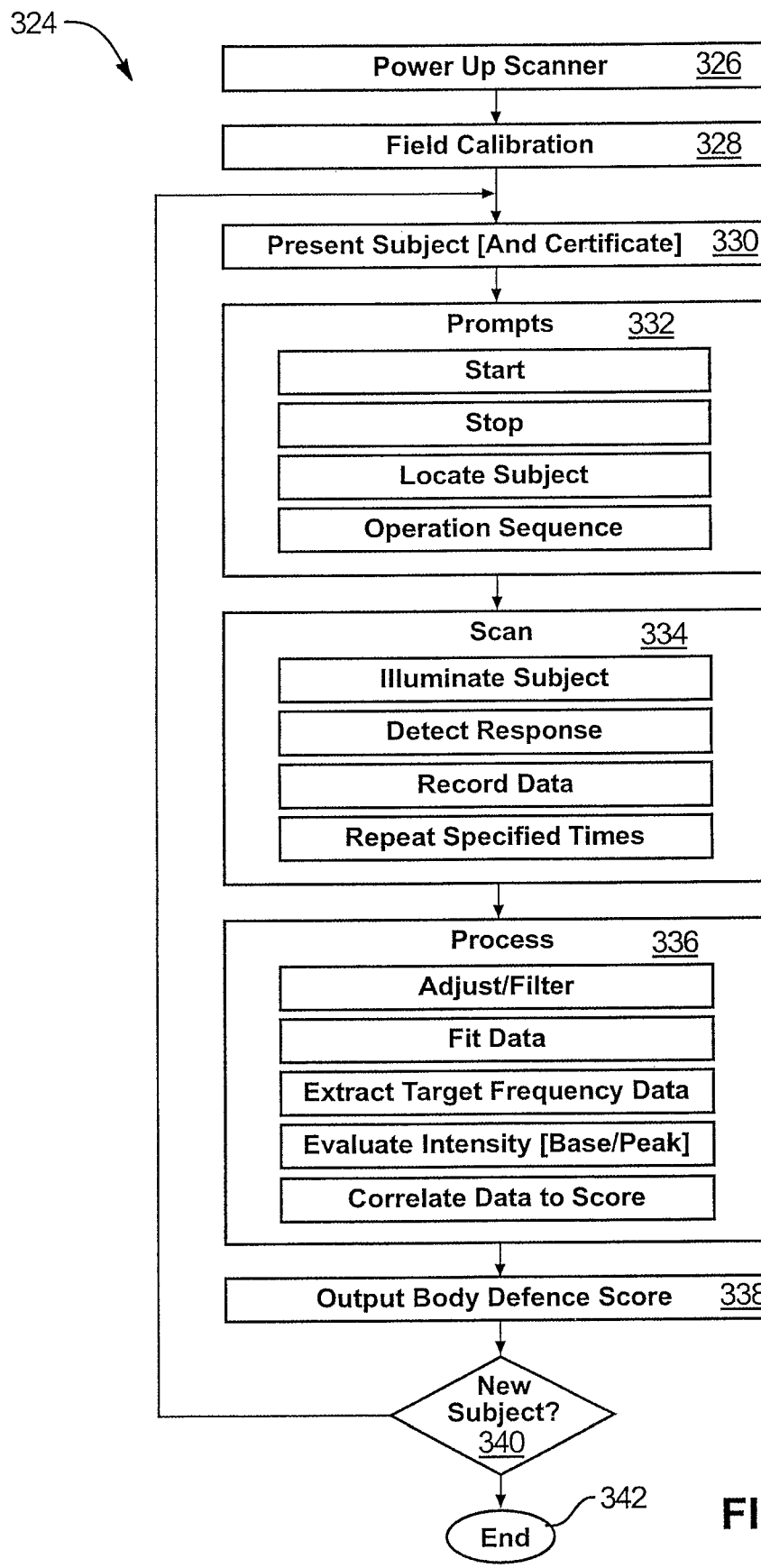
FIG. 12 is a schematic block diagram of one embodiment of a method of operation of a scanner and associated user-interface host connected thereto.

Referring to FIG. 12, operation methods 324 for the scanner 260 may include powering up 326 or turning on 326 the scanner 102. Although certain calibrations occur during manufacture, field calibration 328 may be valuable with each test, or each power up event 326, or periodically over time. Ultimately, field calibration 328 may be required by an operator, or calibration may simply be a hidden and automated process. In some embodiments, the field calibration 328 may be executed by an operator with test samples (surrogate subjects) for measuring the operation, noise, scale, and the like of the scanner 102.

In other embodiments, a scanner 102 may have embedded within it, certain test samples, sequence of events, and a means to illuminate and test calibrated samples in order to set calibration factors. Nevertheless, by whatever means, a field calibration 328 may improve the accuracy and repeatability of readings over time, through different environmental conditions, across different subjects, and so forth.

In general, presentation 330 of a subject may or may not involve presentation of a certificate, shown in brackets as an optional step. That is, a subject may walk into a nutritional supplement or other type store and request a scan to be done as a service at a price. Alternatively, a certificate may be paid for by a party seeking to motivate a subject to obtain a scan and purchase products. The certificate may substitute as financial consideration. The certificate identification provides a traceable number or other symbol for identifying the obligations and payments associated with performing a scan.

The host 100 provides prompts 332. The prompts 332 may include various commands or images to direct the user, subject, or both. For example, indications of starting, locating a subject, or moving a subject's hand or arm closer, further, laterally about, in order to obtain a proper and reliable scan may be provided through prompts 332. Similarly, an operator may be provided indications of steps, waiting periods, operations to be conducted, keys to be struck, and other actions to be taken during, before, after, or in relation to the operation of the scanner. For example, prompted operational sequences may include operation of the scanner 102 as well as interaction with the SCG system 60, or even the sequence of dialing up the home system 60 in order to upload data.

Similarly, browsers, wizards, menus, steps through processes, and the like, may all be implemented with prompts 332 in order to reduce the level of complexity, and the degree of training required. In certain embodiments, the problems 332 may be largely graphical in order to transcend languages, and provide universal information.

A fundamental purpose of the scanner 102 is to scan 334 a subject 104. Accordingly, the scanner 102, among other processes, may illuminate the subject, detect a response (illumination re-radiating or scattering back according to the Raman scattering theory from the subject 104), to provide a detectable result. With delivery of data by the scanner 102 into the host 100, data may be recorded, and the process may be repeated any specified number of times. That is, any given scan 334 of an individual subject 104 may actually involve multiple scans. In one embodiment, 30 scans may be taken over a period of less than 30 seconds in order to get a statistically significant sample of intensities at multiple frequencies across various pixels of a CCD (charge coupled device) or other detector 288.

Similarly, the host 100 will process 336 the information in conjunction with the scanner 102. That is, some pre-processing may occur in a pre-processor 290. Ultimately, filtering may occur within the beams 278, 282, 284, 286, or in signals 289 received from the detector 288. Similarly, filtering may occur through applying software to data. Accordingly, data may be adjusted or filtered or the like. Similarly, data may be fit to a curve in order to provide a statistically reliable integration of the multiple laser scans accomplished within a single scan 334 of a subject 104. That is, multiple scans by a laser source 272 and detector 288 in conjunction with one another actually results in what would be termed a scan 334 of an individual subject 104.

Accordingly, once the data has been fitted, then extraction of the target frequency data may be more useful. That is, after filtering of noise and background, and reducing data by a general curve or histogram of intensities across all frequencies, a frequency of particular interest in detection of carotenoids may be isolated. Accordingly, extraction of data in the target frequency most commonly associated with the Raman scattering or other scattering technique that might be used by a scanner 102, may result in an ability to evaluate the intensity. Of most interest is the base and peak values, for example, of a particular portion of the charted intensity.

One objective is the correlation of the data to a score that is repeatable and meaningful to a subject 104. Accordingly, the correlation process and output on the BDS score or other meaningful output to a user may be part of the processing 336 of the significant data. Thus, an output 338 of a body defense score or other output metric may be done by a printed writing, a displayed image on a screen, a picture, a graph, or the like. If a new subject 104 is to be scanned, then a test 340 may return the process 324 to present 330 subject for scanning. Otherwise, the system may be shut down and end 342 its operation.

Figure 13:
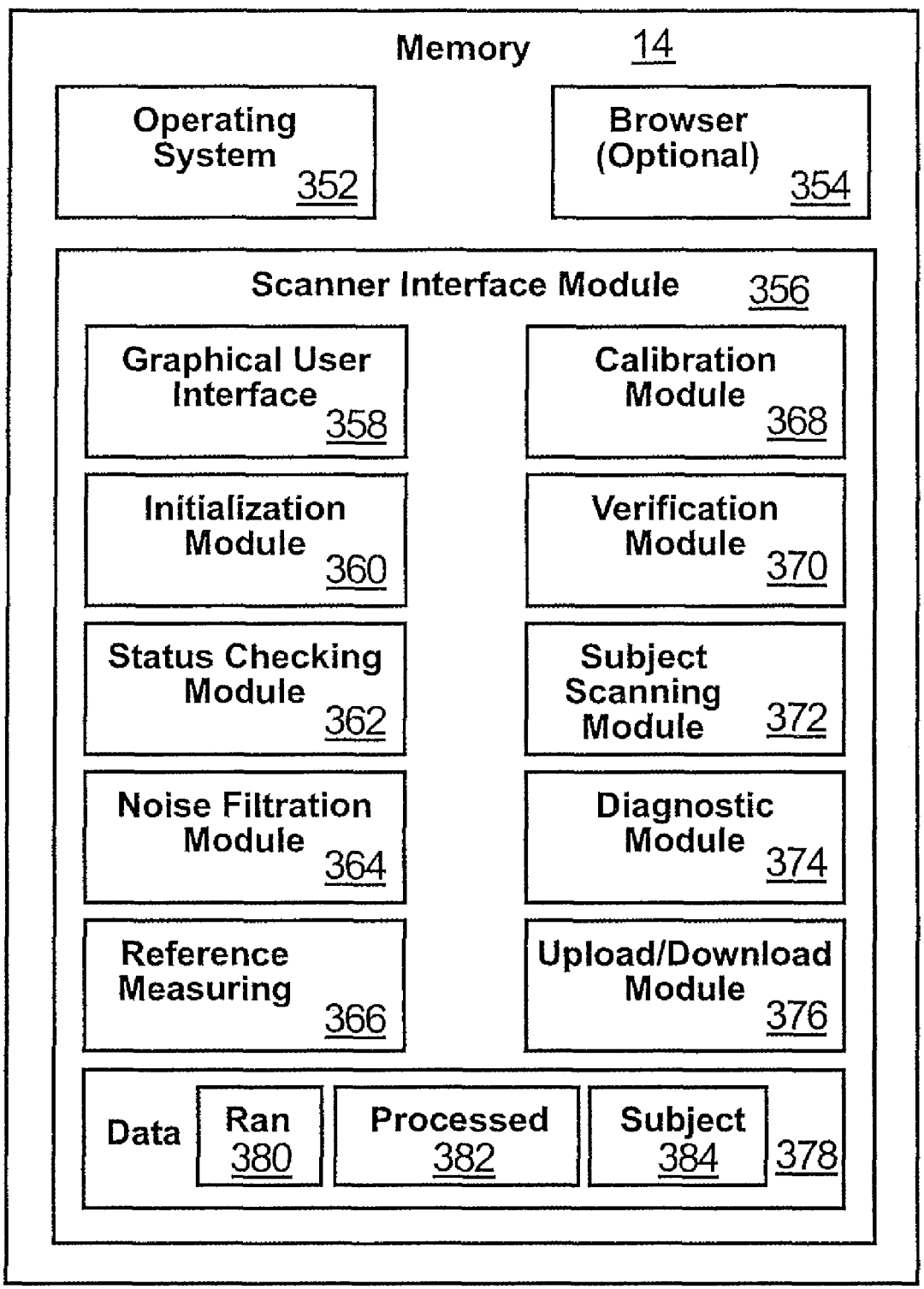
FIG. 13 is a schematic block diagram of one embodiment of a system of modules resident in memory of a computer in order to operate and integrate a system of scanning in accordance with the invention.

Referring to FIG. 13, a user-interface host 100, used to interface a scanner 102 to the global compensation system 60, may be implemented using a laptop, notebook, personal digital assistant, such as a Palm Pilot or Ipaq, a digital tablet, or other dedicated computing device. In certain embodiments, the user-interface host 100 is an independent computing device that is physically separate from the scanner 102. However, in other contemplated embodiments, the user-interface host 100 may be integrated with the scanner 102 into a single device.

The user-interface host 100 may include various memory modules 14, including volatile memory such a RAM, or more permanent memory such as ROM, or magnetic storage such as floppy disks or hard drives. Memory 14 may contain executable and operational data 352, 354, 356 effective to control and operate the scanner 102, provide a graphical interface 358 for an operator, and communicate back to the seamless global compensation system 60.

For example, in certain embodiments, memory 14 may include an operating system 352 to perform basic system tasks, operate a file system, and provide an interface between applications and hardware components. The operating system 352 may be a common operating system 352, such as Windows or Linux, or may be a dedicated operating system 352 designed specifically to operate the scanner 102.

In certain embodiments, memory 14 may optionally include a browser 354. The browser 354 may be used in web-based systems to communicate with a central server 60, or servers 60. The browser 354 may also be used to directly communicate with a dealer portal 86, a consumer portal 88, or other Internet sites.

In accordance with the invention, a scanner interface module 356 may be provided in memory 14 to interface with the scanner 102. For example, a scanner interface module 356 may include a graphical user interface 358 for use by an operator. The graphical user interface 358 may display data to the operator, and may include forms or templates to receive inputs such as subject demographic information, operating variables, and the like.

An initialization module 360 may be used to initialize the scanner 102 before operation. For example, an initialization module 360 may read in parameter files and initialize key coefficients and variables used to operate the scanner 102. Some of these files may be created during a factory calibration process and copied to the user-interface host 100 upon "mating" a scanner 102 thereto. Selected files may be used while operating the scanner 102. Since every scanner 102 may have distinct characteristics and calibration specifications, a serial number may assigned to each scanner 102. When a scanner is operated, the serial number thereof may be compared to serial numbers stored in a configuration file to ensure that files correspond to the scanner 102 connected. Moreover, the initialization module 360 may verify that a scanner 102 is compatible with a version of software used in conjunction therewith.

The initialization module 360 may also initialize one or several communication ports between the user-interface host 100 and the scanner 102. In addition, coefficients and parameters may be read from the scanner's memory for analysis on the user-interface host 100.

A status checking module 362 may be used to retrieve various status from the scanner 102. For example, a status checking module 362 may retrieve the serial number, or other identifying value, of an attached scanner 102 to verify that the scanner 102 is the device originally initialized. Additionally, the status checking module 362 may check various status of the laser 272, such as temperature, or may verify that the scanner 102 is sufficiently "warmed up." Certain returned values may indicate that a scanner 102 is connected and communicating with the user-interface host 100. Other values may indicate that operation parameters are within prescribed limits, thus ensuring that subsequent scans will return accurate and consistent data. The status checking module 362 may be primarily dedicated to checking values of key indicators at any selected point in time.

A noise filtering module 364 may be used to filter noise from data gathered by a scan. For example, in certain embodiments, a "dark scan" may be used to filter noise from subject 104 scans. Raw data values collected during a dark scan may be subtracted from raw data values collected during a subject 104 scan, pixel by pixel, thereby producing a "dark corrected" scan.

The noise filtering module 364 may perform a "dark scan" in response to various conditions. For example, a dark scan may be performed during a warm up period, wherein consistent results from one dark scan followed by another may be used to indicate that a scanner 102 is sufficiently warm and stable. A dark scan may also be performed whenever a scanner 102 is recalibrated. Also, a dark scan may be used if readings appear to be drifting with respect to previous readings. If drift is detected, the results of a scan may be inaccurate. In such a case, a normal scan may be repeated after performing a dark scan.

A reference measuring module 366 may perform scans used in a calibration process. For example, a reference scan may establish variable and coefficient values, such that results (e.g. scores provided to scanned customers) are substantially equivalent to values that would have been produced at the factory. Various routines may be used to verify that the results are reasonably accurate when the new reference values (variable and coefficient values) are used. Other routines may verify that the scanner 102 produces repeatable results that are reasonably constant from scan to scan. If the results are not reasonably constant, the scanner 102 may be considered unreliable. In such cases, the scanner 102 may be locked down such that further scans are prevented, thereby requiring an operator to have the scanner 102 repaired.

A calibration module 368 may be provided to calculate, modify, and test important parameters used in the computation of a subject score. A subject score refers to an assessment or measurement of the health of some aspect of a subject 104 (customer). For example, in accordance with the present invention, a scanner 102 may provide a score indicating the amount of carotenoids present in the skin of a subject 104. However, the score need not refer to carotenoids, but may refer to any measurement or assessment of the health of a patient.

Referring more particularly to scanning for carotenoids, the scanner 102 may compute a score, such as a body defense score of a subject 104. In addition to raw data measured from the subject 104, the score may be calculated using inputs generated by the factory calibration process, the reference measurements 366, and the noise filtering 364. Proper calibration is needed to ensure that a subject 104 is provided with a valid score.

A verification module 370 may be used to verify that a scanner 102 is properly calibrated. For example, a reference material, such as a card or other material having a known concentration or level of carotenoids, may be used to calibrate the scanner 102. The scanner 102 may be calibrated with the reference material at the factory. When recalibrated, the scanner 102 may again measure the concentration in the reference material.

If the measurement is not reasonably close to the original factory reading, the scanner 102 may no longer be producing accurate and consistent results and the scanner 102 may be disabled. This will prevent further scanning and encourage the operator to have the scanner 102 repaired. Since this may be a relatively significant undertaking, it may be desirable to attempt recalibration several times before concluding that the scanner 102 is in need of repair.

A subject scanning module 372 may be responsible for performing scans on subjects 104. For example, the subject scanning module 372 may enable a normal scan on the skin of a subject's hand in order to return a body defense score. The subject scanning module 372 may also verify that the serial number from an attached scanner 102 is the same as the scanner 102 originally initialized to further ensure accuracy of the score. Various operating parameters such as temperature, laser status, and the like, may be checked to verify that the scanner 102 is ready to produce reliable data.

In certain embodiments, the subject scanning module 372 may perform a pre-scan for a prescribed period, such as 20 seconds, to "bleach" the subject's skin. Next, a data acquisition scan may be performed various times, such as 3 times. A body defense score may be calculated after each scan. These scores may be averaged to produce a final body defense score. Only the final body defense score may be presented to a user or operator of the scanner 102. However, each individual body defense score may be saved since these may provide valuable diagnostic information with respect to the functioning of the scanner 102.

Various steps may be performed for each individual scan. For example, an operation may be performed to check for scan transmission errors. The scan may also be "dark corrected" using data calculated by the noise filtering module 364. If excessive luminescence is detected that is out of range of the scanner 102, a scan may be aborted. If a scan is successful, data obtained therefrom may be analyzed to calculate a body defense score. A test may be performed on data received from a scan to determine if there is a significant difference in any of the 3 body defense scores of a subject 104. If a significant difference is detected, an error message may be generated notifying an operator of the excessive spread of values.

A diagnostic module 376 may be provided to diagnose problems, settings, or status of the scanner 102. For example, a diagnostic module may determine or set a communications rate, or baud rate, of the scanner 102. Various commands may be sent to the scanner 102 to monitor the response thereof, in order to ascertain that the scanner 102 is operating correctly.

Other commands may be sent to retrieve the serial number of the scanner 102, or to retrieve the version numbers of scanner firmware and hardware components. Yet other commands may retrieve the temperature, set integration times, set coefficients, turn a laser 272 on or off, return a recently computed body defense score, return raw data, or return peak data computed from raw data.

An upload/download module 376 may function to upload subject data, such as body defense scores or demographic data, to a remote server, such as to the uploaded data files server 76. The module 376 may further coordinate the download, from remote servers such as the software update server 78, of newer versions of software to operate the scanner 102.

The scanner interface module 356 may be further programmed to store data 378. Data 378 may include raw data gathered by the scanner 102, processed data such as body defense scores and the like, and subject data, such as demographic data corresponding to each subject 104.

The present invention may be embodied in other specific forms without departing from its essence or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An apparatus for tracking and distributing royalty payments owed to a licensor for use of a testing device and commission payments owed to operators of the testing device, the apparatus comprising:
   a plurality of testing devices licensed from a licensor thereof, wherein:
      each testing device of the plurality of testing devices is structured to be mobile and independent from one another; and
      each testing device is further configured to measure selected molecular structures in live tissues relating to nutrition of subjects tested thereby and to provide diagnostic information regarding risk of disease and/or risk markers for disease;
   a compensation system configured to upload directly data corresponding to use of the testing devices, the compensation system comprising:
      an authorization server configured to manage and provide authorization to operators of the testing devices prior to operating of the testing devices, and further configured to track use of the testing devices;
      a royalty system configured to allocate royalties due to the licensor based at least in part on use of the testing devices and a royalty schedule; and
      a commission system configured to allocate compensation due to entities responsible for distribution of nutritional products associated with or directed to altering levels of the selected molecular structure in the subjects tested; and
   a communications link operable for connecting each testing device to the compensation system.

2. The apparatus of claim 1, wherein each testing device is further configured to conduct a test comprising measuring tissue of a subject non-invasively, non-destructively, and in vivo, ascertaining the concentration of a selected molecular structure therein, and outputting a value corresponding thereto.

3. The apparatus of claim 1, wherein each testing device is further configured to perform tests by illuminating and measuring a radiant response from live tissue and to determine a corresponding value reflecting concentration of a selected molecular structure relating to nutrition of subjects.

4. The apparatus of claim 1, wherein the selected molecular structures include carotenoids.

5. The apparatus of claim 1, wherein the authorization server is further configured to control operation of one or more of the testing devices.

6. The apparatus of claim 1, wherein the apparatus further comprises a certificate server configured to generate and distribute certificates redeemable for use of the testing devices.

7. The apparatus of claim 6, wherein each certificate includes a certificate number associated therewith.

* * * * *